United States Patent [19]
Lin et al.

[11] Patent Number: 5,284,940
[45] Date of Patent: Feb. 8, 1994

[54] PREPARATION FOR NUCLEIC ACID SAMPLES

[75] Inventors: Lily Lin, Berkeley; Stephen T. Isaacs, Orinda; John E. Hearst, Berkeley, all of Calif.

[73] Assignee: HRI Research, Inc., Concord, Calif.

[21] Appl. No.: 614,921

[22] Filed: Nov. 14, 1990

[51] Int. Cl.$^5$ .................... C07H 23/00; C12Q 1/68; C12N 1/08
[52] U.S. Cl. .................... 536/25.4; 536/25.41; 536/25.42; 435/6; 435/270
[58] Field of Search .................... 435/270, 280, 6, 262, 435/259, 805; 536/27, 28, 25.4, 25.41, 25.42

[56] References Cited

U.S. PATENT DOCUMENTS

| | | |
|---|---|---|
| 3,874,852 | 4/1975 | Hamill . |
| 4,099,917 | 7/1978 | Kim . |
| 4,185,964 | 1/1980 | Lancaster . |
| 4,217,338 | 8/1980 | Quash . |
| 4,286,963 | 9/1981 | Ledis et al. . |
| 4,346,018 | 8/1982 | Carter et al. . |
| 4,419,444 | 12/1983 | Quash . |
| 4,485,175 | 11/1984 | Ledis et al. . |
| 4,521,518 | 6/1985 | Carter et al. . |
| 4,617,275 | 10/1986 | Matsuda et al. . |
| 4,659,678 | 4/1987 | Forrest et al. . |
| 4,683,195 | 7/1987 | Mullis et al. . |
| 4,683,202 | 7/1987 | Mullis . |
| 4,745,071 | 5/1988 | Lapicola et al. . |

OTHER PUBLICATIONS

Tsutsui and Mueller, BBRC 149:628 (1987).
Scher et al., Can. Res. 48:6278 (1988).
Byrnes et al., Biochem. 14:796 (1975).
Erlich, H. A. (ed.), *PCR Technology*, Stockton Press, p. 33 (1989) p. 261.
Hronis and Traugh, J. Biol. Chem. 261:6234 (1986.
Hershko et al., Proc. Nat. Acad. Sci. USA 81:1619 (1984).
Waxman et al., J. biol. Chem. 260:11994 (1985).
Tsutsui and Mueller, J. Biol. Chem. 257:3925 (1982).
Paabo et al., Nucl. Acids Res. 16:9775 (1988).
Longley and Stewart, J. Immunol. Methods 121:33 (1989).
Kacian et al., Proc, Nat. Acad. Sci. USA 69:3038 (1972).
Chamberlin et al., Nature 228:227 (1970).
Wu and Wallace, Genomics 4:560 (1989).
Bajorath et al., Nature 337:481 (1989).
Innis et al. (eds.), *PCR Protocol: A Guide to Methods and Applications* (1990), pp. 159–166, 261–271.
Schacter, Sem. in Hem. 25:349 (1988).
Yoshinaga et al., J. Biol. Chem. 257:7778 (1982).
Kutty and Maines, J. Biol. Chem. 257:9944 (1982).
Yoshida et al., J. Biol. Chem. 75:1187 (1974).
Paabo et al. Nucleic. Acid. Res. 16(20):9775 (1988).
Manialis et al "Molecular Cloning.": Isolation of High Molecular Weight Eukariotic DNA from Cells pp. 280–290 (1982).
Byrnes. et al. Biochem 14(4): 796 (1975).
Van Atta et al. Biochem 29(20) 4783 (1990).
Pasternack. et al. Biochem 22(23) 5409 (1983).

*Primary Examiner*—Robert A. Wax
*Assistant Examiner*—Miguel J. Escallon
*Attorney, Agent, or Firm*—Haverstock, Medlen & Carroll

[57] ABSTRACT

Methods and compounds for the preparation of nucleic acid samples. Polymerase inhibitors are treated so as to allow for amplification of nucleic acid from biological sources, including whole blood.

7 Claims, 26 Drawing Sheets

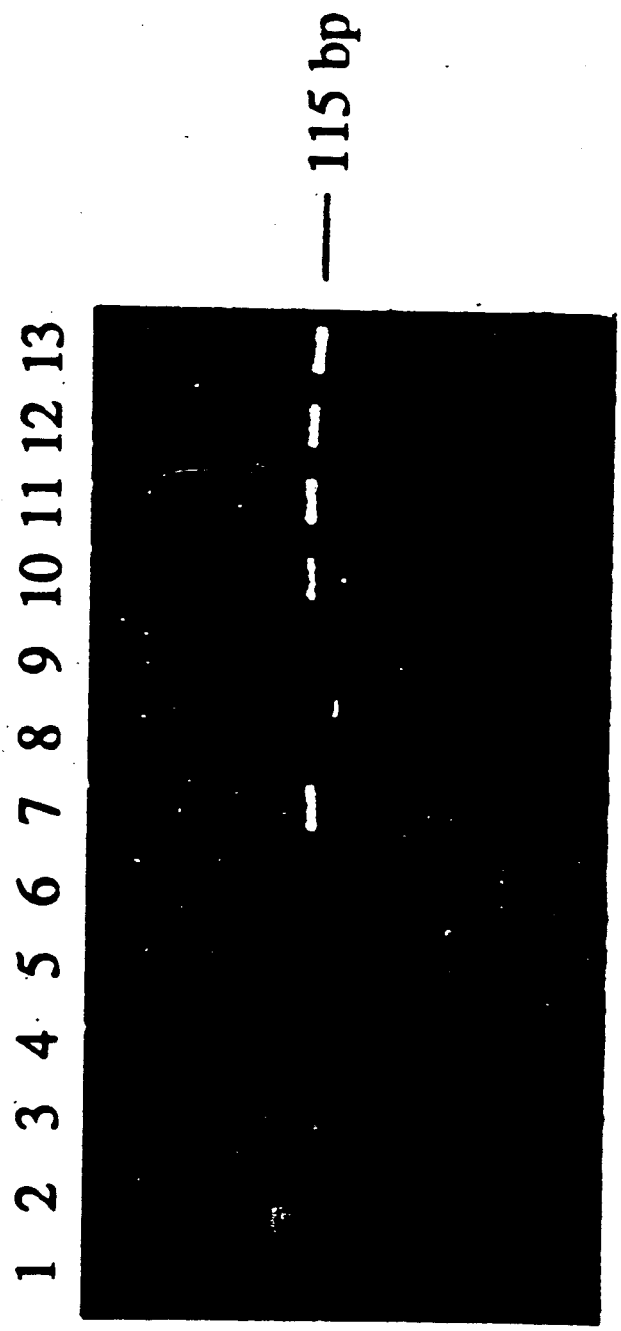

FIGURE 10
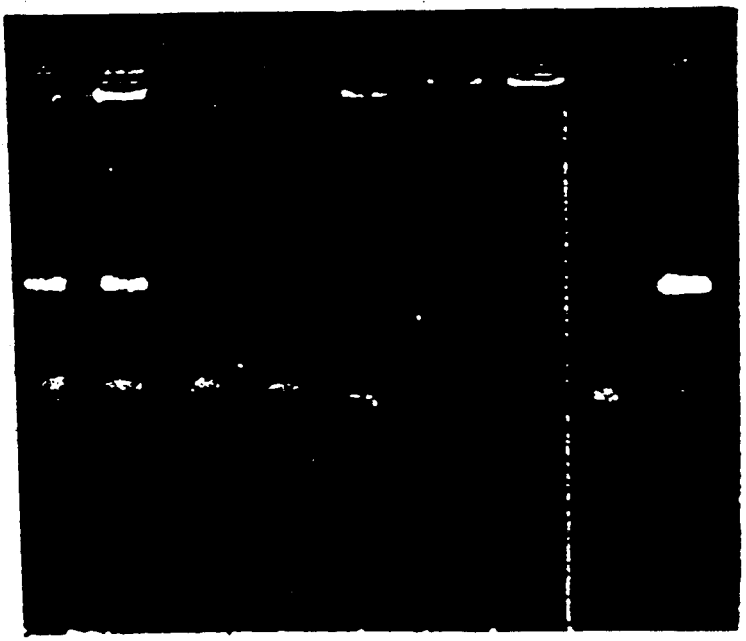
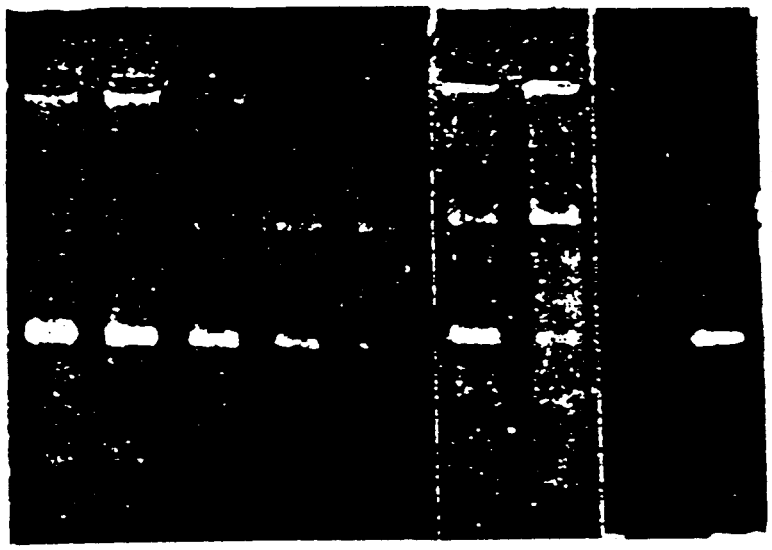

FIGURE 11
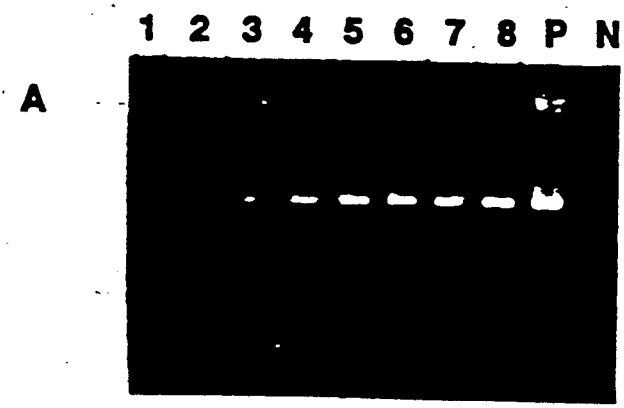
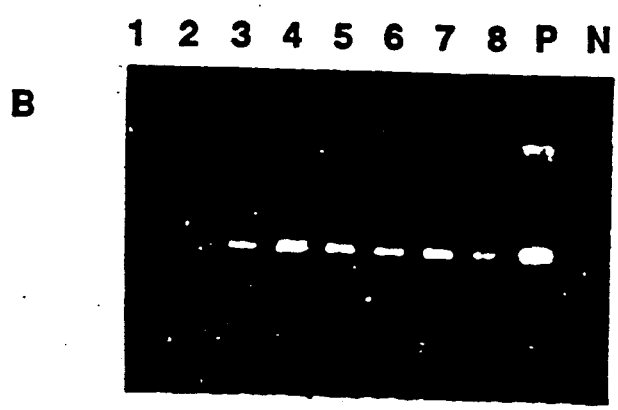

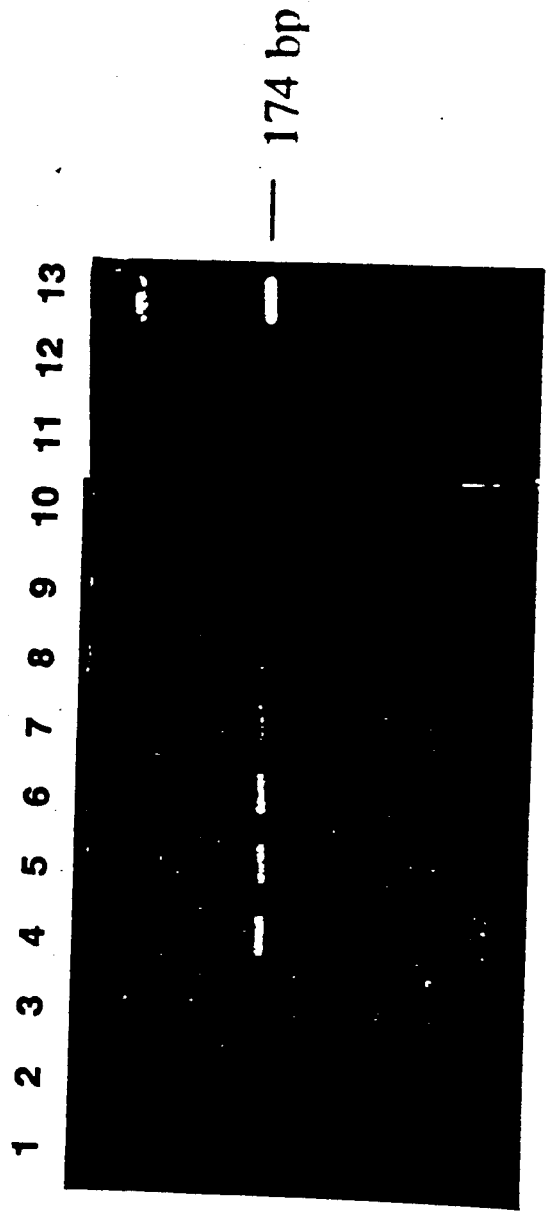

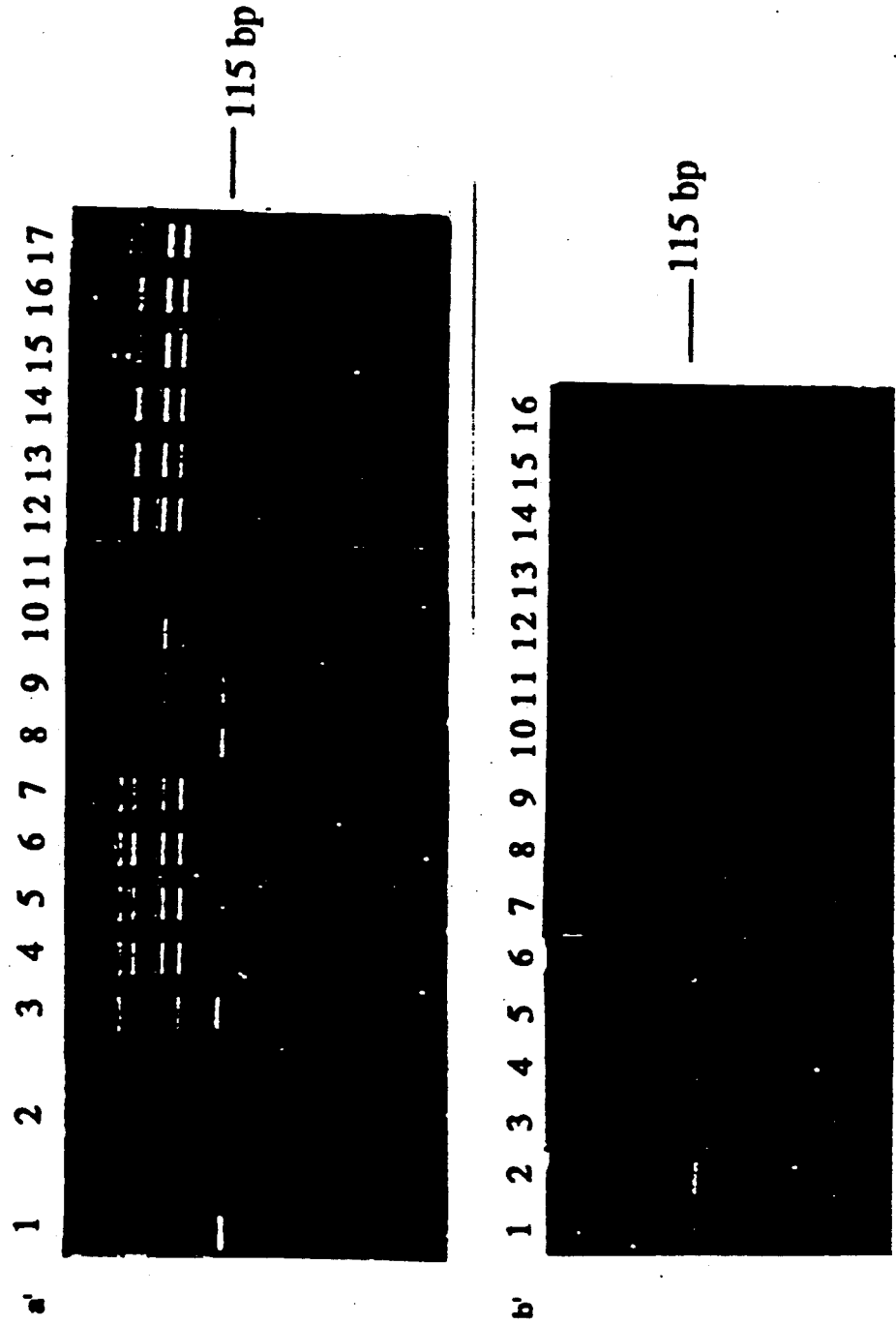

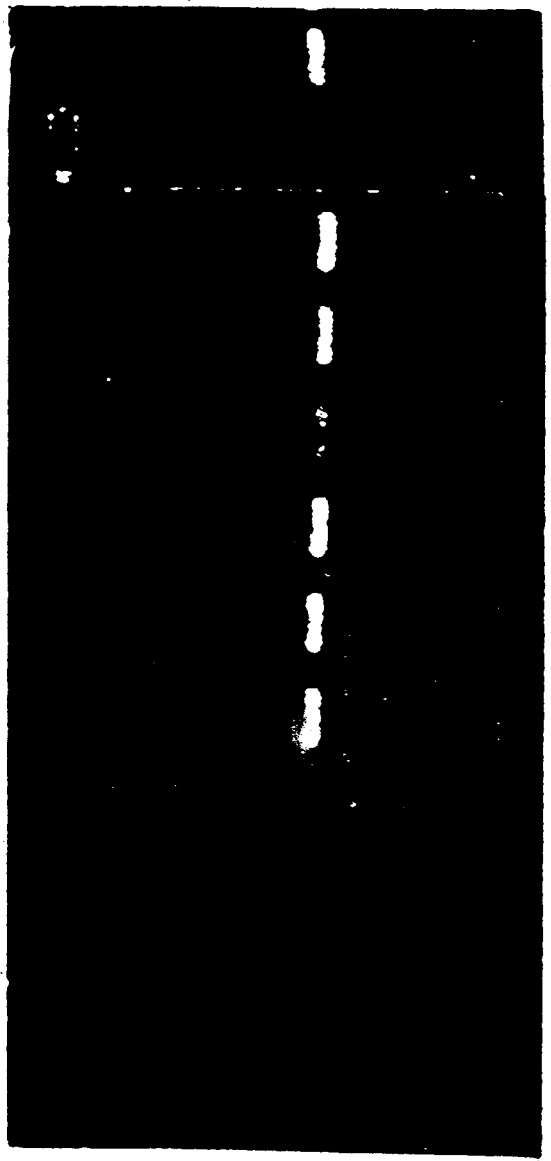

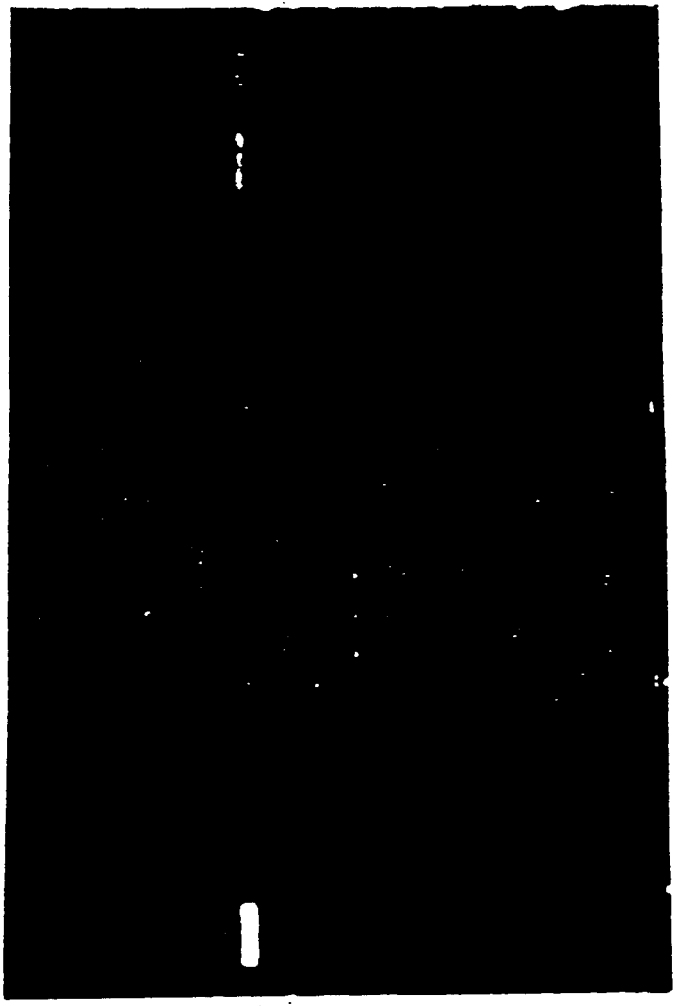

PREPARATION FOR NUCLEIC ACID SAMPLES

DESCRIPTION

1. Field of the Invention

The present invention relates to methods and compounds for the preparation of nucleic acid samples.

2. Background

Nucleic acid technology has made possible the manipulation, amplification, selection and characterization of a potentially very large number of eukaryotic, prokaryotic and viral genes. The vast majority of nucleic acid assays, whether involving manipulation, amplification, selection or characterization, are performed using nucleic acid that has been isolated or separated from its source (e.g. isolated from cells, separated from proteins, etc.). This approach has the advantage that potential problems from non-nucleic acid components of the source is avoided. This approach, however, has the disadvantage that great effort and expense may be involved in isolation or separation procedures.

Problems in nucleic acid assays from non-nucleic acid components of the nucleic acid source are well-known. One common source of nucleic acid exhibiting problems is whole blood. Almost one half the volume of whole blood is occupied by cells, which consist largely of red blood cells (normal range: $4.2-6.1 \times 10^6/ul$), much smaller numbers of white blood cells (normal range: $4.8-10.8 \times 10^3/ul$) and platelets (normal range: $130-400 \times 10^3/ul$). The liquid portion, the blood plasma, is 90% water. The major plasma constituents include plasma proteins, organic metabolites and waste products, and inorganic components (Hematology, 2nd ed., W. J. Williams, et al., ed., McGraw-Hill, N.Y., 1977). Any one of these constituents may create difficulties with nucleic acid assays.

One class of constituents known to inhibit nucleic acid associated enzymes are the "hemes" which include hemin and hematin. Hemin has been reported to inhibit virion-associated reverse transcriptase (RTase) of murine leukemia virus (MuLV) (Tsutsui and Mueller, BBRC 149, 628-634, 1987), DNA ligase (Scher et al., Can. Res. 48, 6278-6284, 1988), cytoplasmic DNA polymerase (Byrnes et al., Biochem. 14, 796-799, 1975) Taq polymerase (*PCR Technology*, H. A. Erlich (ed.) Stockton Press (1989) p.33), and other enzymatic systems that utilize ATP as a cofactor such as the hemin-controlled protein kinase that affects protein synthesis (Hronis and Traugh, J. Biol. Chem. 261, 6234-6238, 1986), the ATP-dependent ubiquitin-dependent protease pathway (Hershko et al., PNAS USA 81, 1619-1623, 1984), and the ATP-dependent ubiquitin-independent protease pathway (Waxman et al., J. Biol. Chem. 260, 11994-12000, 1985).

Freshly-made hemin solution inhibited MuLV RTase activity by 50% at a hemin concentration of 10 $\mu M$. Aged hemin solutions (5 days at room temperature) inhibited MuLV RTase by 50% at 0.1 $\mu M$ concentration. Addition of 4-fold excess MuLV RTase caused an increase of enzyme activity in the presence of hemin while addition of excess template did not. Addition of a heme-binding protein from rabbit serum (Tsutsui and Mueller, J. Biol. Chem. 257, 3925-3931, 1982) completely restored enzyme activity. This suggests that hemin is a reversible inhibitor of MuLV RTase and that its interaction with the enzyme is noncovalent in nature. Hemin does not inhibit the activity of reverse transcriptase purified from avian myeloblastosis virus.

Experiments with DNA ligase indicate that hemin at 4 $\mu M$ or less does not affect DNA ligase activity or DNA substrate integrity. Scher et al., Can. Res. 48, 6278-6284, 1988. Pre-incubations of DNA ligase with hemin led to half-maximal inhibition of DNA ligase at hemin concentrations of 25-100 $\mu M$ (depending on the source of the DNA ligase). NAD-dependent DNA ligase from E.coli was not inhibited by hemin at concentrations up to 150 $\mu M$. The inhibition of T4 DNA ligase activity and DNA ligase from mouse erythroleukemia (MEL) cells was not reversible by dilution, dialysis, or sucrose gradient centrifugation of cell-free extracts. Incubation of DNA ligase from MEL cells with hemoglobin was not inhibitory.

Binding assays demonstrate that hemin prevents association and causes dissociation of the DNA-cytoplasmic DNA polymerase complex. Hemin at a concentration of 12 $\mu M$ or higher completely inhibits the formation of DNA-enzyme complex. Byrnes et al., Biochem. 14, 796-799, 1975. This report also shows that hemin inhibition of DNA synthesis is competitive with respect to template and noncompetitive with respect to substrate. Furthermore, inhibition could be reversed by either 1) addition of globin to the polymerase-containing reaction mixture prior to the addition of hemin to the reaction mixture, or 2) addition of globin to hemin followed by addition of this mixture to the polymerase-containing reaction mixture. Inhibition could not be reversed by the addition of globin after introduction of hemin to the polymerase-containing reaction mixture Experiments with purified hematin and related compounds have shown that they are potent inhibitors of Taq polymerase. Taq polymerase is used in the amplification procedure described by K. B. Mullis et al., U.S. Pat. Nos. 4,683,195 and 4,683,202. This amplification procedure is a method for increasing the concentration of a segment of a target sequence in a mixture of genomic DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing, and polymerase extension can be repeated many times (i.e. denaturation, annealing and extension constitute one "cycle;" there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to by the inventors as the "Polymerase Chain Reaction" (hereinafter PCR). Because the desired amplified segments of the target sequence become the predominant sequences (in terms of concentration) in the mixture, they are said to be "PCR amplified".

Hematin is inhibitory to PCR at a final concentration of 0.8 μM or higher (*PCR Technology*, H. A. Erlich (ed.) Stockton Press (1989) p. 33). "Protoporphyrin" is inhibitory at 20 μM. Non-heme blood components such as globin, Fe++ and Fe+++ ions also inhibit PCR (Walsh et al.).

Where the inhibitor is a competitive inhibitor, one approach is to add more reagent and "swamp" the inhibition. This has been attempted in the case of PCR inhibition. Walsh et al. have shown that, while hematin inhibition cannot be overcome by additional quantities of template DNA, it can be overcome by additional quantities of Taq polymerase or primer.

This swamping approach has a serious disadvantage: additional quantities of reagents may cause spurious results. Indeed, in the case of PCR it is known that additional quantities of Taq polymerase or primers can result in nonspecific amplification products. S. Paabo et al., Nucleic Acids Res. 16:9775 (1988). These nonspecific products are believed to be due to weak priming sites.

The conventional method for the preparation of amplifiable nucleic acid from whole blood involves isolation of lymphocytes by density gradient centrifugation. This typically involves the isolation of T4 enriched white blood cells by centrifugation through a Ficoll gradient. See e.g. Longley and Stewart, J. Immunol. Methods, 121, 33-38, 1989. The red blood cells and granulocytes pellet in this system. The lymphocyte-enriched white blood cells are recovered from the gradient interface. To remove Ficoll, which inhibits Taq polymerase, the cells are usually washed one or more times by centrifuging and removing the supernatant. Although this procedure yields lymphocytes free of red blood cells and most of the platelets, there are a number of disadvantages to this procedure, including: (1) relatively large, freshly drawn blood samples must be layered over Ficoll carefully so that the interface is undisturbed; (2) lymphocytes must be collected (after centrifugation) by removing the opaque band of cells located at the gradient interface and, (3) the collected lymphocytes must be washed free of Ficoll. The careful layering of blood is a slow and somewhat artful step. The collection of the cells at the gradient interface demands that i) enough blood be used initially such that the cells can be seen with the naked eye, ii) the cells be captured in a pipette (a cumbersome and low-yield technique), and iii) amplification be carried out in a different reaction vessel from that used to layer the blood. Finally, the approach utilizes a polymerase inhibitor (i.e. Ficoll) in large amounts that is not easily removed except by centrifugation. These drawbacks have seriously hindered the application of amplification techniques to large-scale clinical diagnostics.

SUMMARY OF THE INVENTION

The present invention offers a radical change from the cumbersome nucleic acid whole blood method of density centrifugation and provides a flexible approach to whole blood processing for nucleic acid amplification. Importantly, the method of whole blood processing of the present invention can be carried out with i) only microliter amounts of blood (e.g. fingerstick or heelstick), ii) stored blood (including dried blood), and iii) the same, single reaction vessel used for amplification (allowing for quantitative recovery of cellular nucleic acid). Because of these features, the method of the present invention is also amenable to automation.

In one embodiment, the present invention comprises a method for preparing nucleic acid samples comprising the steps of a) providing nucleic acid in blood cells from a biological source containing one or more polymerase inhibitors; b) lysing said blood cells to make a lysate containing said nucleic acid; and c) treating said lysate to inactivate at least one of said polymerase inhibitors.

In another embodiment, the present invention comprises a method for preparing nucleic acid samples comprising the steps of a) providing nucleic acid in blood cells from a biological source containing one or more polymerase inhibitors; b) concentrating said blood cells; c) lysing said concentrated blood cells to make a lysate containing said nucleic acid; and d) treating said lysate to inactivate at least one of said polymerase inhibitors.

In still another embodiment, the present invention comprises a method for preparing nucleic acid samples comprising the steps of a) providing whole blood comprising red cells, white cells, and one or more polymerase inhibitors, said white cells containing nucleic acid; b) lysing said red blood cells selectively to make a first lysate; c) concentrating said white blood cells; and d) lysing said white blood cells to make a second lysate containing said nucleic acid.

Lysis typically comprises adding a lysing agent to said blood cells. The lysing agent in some cases is an enzyme, such as a protease. Where it is a protease, the lysis further comprising the step of inactivating said enzyme.

In one embodiment, the present invention contemplates that inhibition treatment is achieved using an interfering reagent. In one embodiment, the interfering reagent comprises a porphyrin-binding compounds. In another embodiment the interfering reagent comprises a compound selected from the group consisting of globin, serum albumin, and transferrin. The present invention contemplates an embodiment where the interfering reagent comprises serum albumin and one or more cofactors, as well as where the interfering reagent comprises transferrin and one or more cofactors. When serum albumin is used, it is preferred that the cofactor is selected from the group consisting of bicarbonate ion, azide ion, thiocyanate ion, cyanate ion, oxalate ion, malonate ion, glycinate ion, thioglycolate ion, and salts thereof. When transferrin is used, it is preferred that the cofactor is selected from the group consisting of bicarbonate ion, thiocyanate ion, cyanate ion, glycinate ion, thioglycolate ion, and salts thereof.

In some embodiments the concentrating step comprises immobilizing said blood cells on a support. The concentrating may further comprise drying said immobilized blood cells. In some embodiments, the support is absorptive.

In other embodiments, the concentrating comprises centrifuging a first lysate to create a pellet of said white cells and a supernatant. Thereafter, concentrating further comprises removing said supernatant. Lysis can thereafter be achieved by adding a lysing agent to said white blood cell pellet.

In still other embodiments, concentrating comprises filtering a first lysate to isolate and immobilize white cells. Thereafter, the lysis comprises adding a lysing agent to said immobilized blood cells on said support. In this case, the preferred lysing agent comprises an enzyme, such as a protease. Again, it is preferred that the enzyme be later inactivated.

In some embodiments, selective lysis is performed wherein said selective lysis comprises adding a selective lysing agent to said blood cells. A preferred selective lysing agent comprises one or more quaternary ammonium salts.

The method of the present invention, in some embodiments, further comprises the step of amplifying said nucleic acid.

The present invention also contemplates an apparatus for automating the methods of the present invention. In one embodiment, the present invention contemplates an apparatus for preparing nucleic acid samples comprising a) means for containing nucleic acid in blood cells from a biological source having one or more polymerase inhibitors; b) means for lysing said blood cells to make a lysate containing said nucleic acid; and c) means for treating said lysate to inactivate at least one of said polymerase inhibitors.

In another embodiment, the present invention contemplates an apparatus for preparing nucleic acid samples comprising a) means for containing nucleic acid in blood cells from a biological source having one or more polymerase inhibitors; b) means for concentrating said blood cells; c) means for lysing said concentrated blood cells to make a lysate containing said nucleic acid; and d) means for treating said lysate to inactivate at least one of said polymerase inhibitors.

In still another embodiment, the present invention contemplates an apparatus for preparing nucleic acid samples comprising a) means for providing whole blood comprising red cells, white cells, and one or more polymerase inhibitors, said white cells containing nucleic acid; b) means for lysing said red blood cells selectively to make a first lysate; c) means for concentrating said white blood cells; and d) means for lysing said white blood cells to make a second lysate containing said nucleic acid.

The present invention also contemplates an apparatus having a means for amplifying said nucleic acid in said lysate.

The present invention also contemplates methods for amplification. In one embodiment, the present invention contemplates, a method for nucleic acid amplification comprising the steps of a) providing in any order; i) a nucleic acid sample containing at least one amplifiable nucleic acid sequence in a solution containing polymerase inhibitors, ii) all standard reagents necessary to amplify at least a portion of said nucleic acid sequence, iii) at least one amplification enzyme capable of initiating an amplification reaction resulting in a nucleic acid product, iv) an interfering reagent in an amount sufficient to overcome the inhibition by said polymerase inhibitors of said amplification enzyme so as to increase the amount of said nucleic acid product obtained from said nucleic acid sample by the amplification reaction; b) adding in any order: said nucleic acid sample, said amplification reagents, and said interfering reagent, so as to form a reaction mixture; and c) adding said amplification enzyme to said reaction mixture.

The present invention also contemplates a nucleic acid amplification reaction mixture composition comprising i) a nucleic acid sample containing at least one nucleic acid sequence of interest in a solution containing polymerase inhibitors, ii) all standard reagents necessary to amplify at least a portion of said nucleic acid sequence, iii) at least one amplification enzyme, iv) at least one interfering reagent in an amount sufficient to overcome the inhibition by said polymerase inhibitors of said amplification enzyme so as to increase the amount of nucleic acid product obtained from said nucleic acid sample by the amplification reaction.

The present invention also contemplates a method of obtaining amplified deoxyribonucleic acid from ribonucleic acid, comprising the steps of a) providing, in any order, a ribonucleic acid sample from a biological source containing deoxyribonucleic acid polymerase inhibitors, reverse transcriptase, one or more interfering reagents, a deoxyribonucleic acid polymerase, and a reaction vessel; b) adding, in any order, ribonucleic acid and reverse transcriptase to said reaction vessel, so as to make deoxyribonucleic acid sequences; b) adding an interfering reagent to said reaction vessel; c) adding said deoxyribonucleic acid polymerase to said reaction vessel so as to amplify said deoxyribonucleic acid sequences.

DESCRIPTION OF THE DRAWINGS

FIG. 2A is a (direct print) photograph of an ethidium bromide stained gel of electrophoresed PCR-amplified HIV sequences following chemical reduction of hematin. (Direct printing results, in light bands on a dark background).

FIG. 3A is a (direct print) photograph of an ethidium bromide stained gel of electrophoresed PCR-amplified HIV sequences following photochemical treatment of biliverdin. FIGS. 3B-1, 3B-2 and 3B-3 shows absorption spectra of biliverdin following photochemical treatment over time.

FIGS. 4B-1, 4B-2, 4B-3 and 4B-4 shows absorption spectra of bilirubin following photochemical treatment over time.

FIGS. 10A and 10B are a (direct print) photographs of an ethidium bromide stained gel of electrophoresed PCR-amplified HIV sequences following the steps of Mode Ib (see FIG. 1) of the method of the present invention.

FIGS. 11A and 11B are (direct print) photographs of an ethidium bromide s gel of electrophoresed PCR-amplified HLA Class II gene sequences following the steps of Mode Ib (see FIG. 1) of the method of the present invention.

FIG. 13 is a (direct print) photograph of an ethidium bromide stained gel of electrophoresed PCR-amplified, globin gene sequences following the steps of Mode III (see FIG. 1) of the method of the present invention.

FIGS. 14A-A' and 14A-B' are (direct print) photographs of an ethidium bromide stained gel of electrophoresed PCR-amplified HIV sequences comparing the specificity and sensitivity of amplifications following the steps of Mode Ib and Mode III (see FIG. 1) of the method of the present invention.

FIG. 15 is a (direct print) photograph of an ethidium bromide stained gel of electrophoresed PCR-amplified, HIV sequences following biochemical inhibitor treatment according to one embodiment of the method of the present invention.

DESCRIPTION OF THE INVENTION

Figure 1:
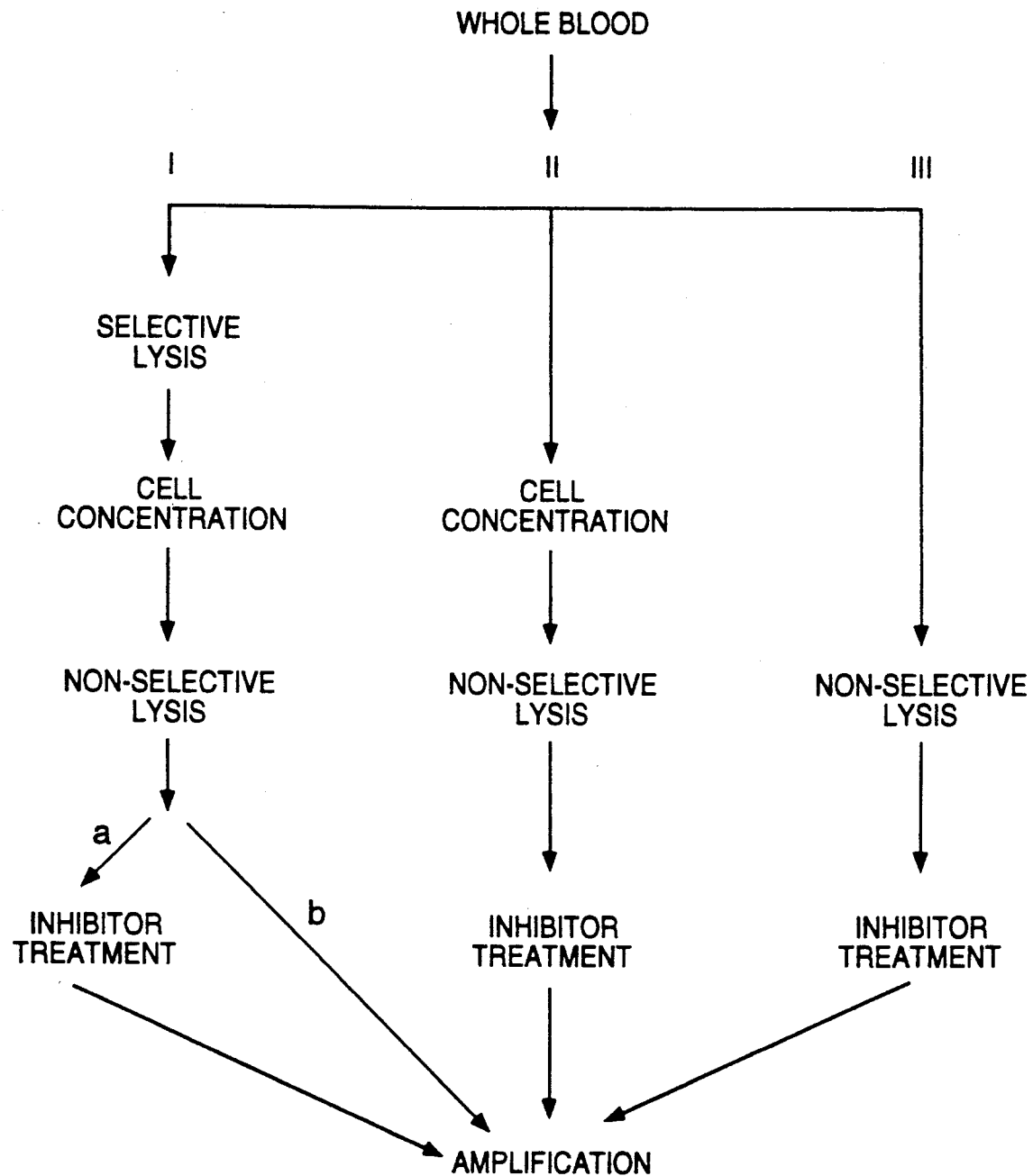
FIG. 1 schematically shows embodiments of the method of the present invention for processing whole blood for amplification.

The present invention provides a method to both isolate nucleic acid sequences from biological sources and to neutralize any agents that might inhibit further manipulation of the concentrated nucleic acid sequences. By "biological source" it is meant that the nucleic acid to be concentrated is in a tissue or bodily fluid. While the preferred biological source of the present invention is whole blood, it is not intended that the present invention be limited to this source alone. The present invention contemplates concentrating nucleic acid sequences from other biological sources as well (e.g. bone marrow, spinal fluid, urine, feces, and tissue of all types, including biopsied tissue). The present invention further contemplates concentrating nucleic acid sequences from blood cells found in biological sources other than whole blood (.e.g. lymphocytes in sputum, urine, etc.). The present invention further contemplates concentrating nucleic acid sequences from the remains or residue of biological sources (e.g. forensic and archeological specimens).

It should be stressed that it is not intended that the present invention be limited to preparation of nucleic acid for amplification. The present invention has applicability at any point that preparation of nucleic acid samples is desired. Nonetheless, the present invention has particular applicability when amplification is desired (whether deoxyribonucleic acid or ribonucleic acid amplification).

It should be stressed that it is not intended that the present invention be limited to any particular amplification technique. "Amplification" is a special case of nucleic acid replication involving template specificity. It is to be contrasted with non-specific template replication (i.e. replication that is template-dependent but not dependent on a specific template). Template specificity is here distinguished from fidelity of replication (i.e. synthesis of the proper polynucleotide sequence) and nucleotide (ribo- or deoxyribo-) specificity. Template specificity is frequently described in terms of "target" specificity. Target sequences are "targets" in the sense that they are sought to be sorted out from other nucleic acid. Amplification techniques have been designed primarily for this sorting out. Template specificity is achieved in most amplification techniques by the choice of enzyme. Amplification enzymes are enzymes that, under conditions they are used, will process only specific sequences of nucleic acid in a heterogenous mixture of nucleic acid. For example, in the case of Q$\beta$ replicase, MDV-1 RNA is the specific template for the replicase. D. L. Kacian et al., Proc. Nat. Acad. Sci USA 69:3038 (1972). Other nucleic acid will not be replicated by this amplification enzyme. Similarly, in the case of T7 RNA polymerase, this amplification enzyme has a stringent specificity for its own promoters. M. Chamberlin et al., Nature 228:227 (1970). In the case of T4 DNA ligase, the enzyme will not ligate the two oligonucleotides where there is a mismatch between the oligonucleotide substrate and the template at the ligation junction. D. Y. Wu and R. B. Wallace, Genomics 4:560 (1989). Finally, Taq polymerase, by virtue of its ability to function at high temperature, is found to display high specificity for the sequences bounded and thus defined by the primers; the high temperature results in thermodynamic conditions that favor primer hybridization with the target sequences and not hybridization with non-target sequences. *PCR Technology*, H. A. Erlich (ed.) (Stockton Press 1989).

Some amplification techniques take the approach of amplifying and then detecting target; others detect target and then amplify probe. Regardless of the approach, nucleic acid must be free of inhibitors for amplification to occur at high efficiency.

"Amplification reagents" are defined as those reagents (primers, deoxyribonucleoside triphosphates, etc.) needed for amplification except for nucleic acid and the amplification enzyme. Typically, amplification reagents along with other reaction components are placed and contained in a reaction vessel (test tube, microwell, etc.).

"Polymerase inhibitors" include all compounds (organic and inorganic) that reduce the amount of nucleic acid replication by enzymes. It is not intended to be limited by the mechanism by which inhibitors achieve this reduction. Furthermore, it is not intended to be limited to only those inhibitors which display large reductions.

The present invention offers a radical change from the cumbersome nucleic acid whole blood method of density centrifugation and provides a flexible approach to whole blood processing for nucleic acid amplification (see FIG. 1). Importantly, the method of whole blood processing of the present invention can be carried out with i) only microliter amounts of blood (e.g. fingerstick or heelstick), ii) stored blood (including dried blood), and iii) the same, single reaction vessel used for amplification (allowing for quantitative recovery of cellular nucleic acid, in contrast, to the low-yield density centrifugation method). Because of these features, the method of the present invention is also amenable to automation.

In one mode ("Mode I"), the present invention offers a selective cell lysis step that involves lysing red blood cells in whole blood or diluted whole blood under conditions which leave white blood cells and/or their nuclei intact. Thereafter, a process step is performed that involves concentration of the cells. "Concentration" is defined broadly and may result from a wide variety of techniques, including filtration, agglutination, centrifugation, immobilization, and/or fluid evaporation. Following the concentration step, there is another lysis step. Since the red cells are gone, the lysis need not be selective and is therefore referred to as "non-selective" lysis. However, the present invention contemplates the use of selective reagents in the non-selective lysis step as well. At this point, Mode I may or may not have another step before amplification. In one version ("a"), the method proceeds to an inhibitor treatment step. By "inhibitor treatment" it is meant that a process is carried out to treat potential, residual polymerase inhibitors such as heme and its related compounds. The process may be chemical, biochemical, photochemical, immunological, or enzymatic, or any combination thereof (e.g. enzymatic followed by photochemical; chemical followed by enzymatic; chemical followed by photochemical). In another version ("b"), the method proceeds directly to amplification.

In another mode ("Mode II"), the present invention offers a concentration step followed by a non-selective lysis step, which in turn is followed by an inhibitor treatment step prior to amplification. In still another mode ("Mode III"), a non-selective cell lysis step is used followed by an inhibitor treatment step prior to amplification. Again, each of these steps is defined broadly (see definitions above). Each of these modes, and the numerous embodiments for each of these modes, are described in detail below.

Mode I

Selective Cell Lysis. The present invention contemplates a selective cell lysis step that involves lysing red blood cells in whole blood or diluted whole blood under conditions which leave white blood cells and/or their nuclei intact. The present invention contemplates a wide variety of selective lysing agents. For example, the present invention contemplates selective lysis by the use of agents such as saponin, dilute hydrochloric acid, ammonium chloride, and detergents such as Triton X-100. These agents are commercially available. The present invention further contemplates the use of detergent along with isotonic saline as described by Kim, U.S. Pat. No. 4,099,917, hereby incorporated by reference. The present invention further contemplates selective lysis using water as well as selective lysis by freezing and thawing.

The preferred selective lysing agent of the present invention is one utilizing quaternary ammonium salts. Quaternary ammonium salts can advantageously be employed as a stromatolysing agent, with the virtually instantaneous destruction of red blood cells but yet without destruction of white blood cells. The quanternary ammonium ion in the salt is of the type having three short chain alkyl groups and one long chain alkyl group attached to nitrogen. Referring to the short chain alkyl groups as $R_1$, $R_2$, and $R_3$, these may have from 1 to 4 carbon atoms, as represented by methyl, ethyl, propyl, and butyl. Referring to the long chain alkyl group as $R_4$, this may vary in the range of about 10 to 20 carbon atoms (from decyl to eicosyl). For example, trimethyl tetradecyl ammonium halides are described by Hamill, U.S. Pat. No. 3,874,852, hereby incorporated by reference. Ledis et al., U.S. Pat. Nos. 4,485,175 and 4,286,963, hereby incorporated by reference, also describe a number of known selective cell lysing agents which contain quaternary ammonium halides. The lytic solutions may contain potassium cyanide, sodium nitrite or sodium nitroferricyanide. On the other hand, a cyanide ion-free lysing agent may used as described by Lancaster et al., U.S. Pat. No. 4,185,964, hereby incorporated by reference. Other quaternary ammonium salt-containing lysis agents may be employed in the selective lysis step of the present invention. See e.g. Carter et al., U.S. Pat. Nos. 4,346,018 and 4,521,518, Larsen, U.S. Pat. No. 4,521,518, Matsuda et al., U.S. Pat. No. 4,617,275, and Lapicola et al., U.S. Pat. No. 4,745,071, hereby incorporated by reference.

Commercial, quaternary ammonium salt-containing lysis agents are available from Sequoia-Turner Corporation (Mountain View, Calif., U.S.A.). These agents lyse red blood cells instantly and break down red cell fragments and their stroma or ghosts. Whole blood may be diluted (1:10 or more) with diluent containing white blood cell stabilizing agents such as 1,3-dimethylurea before treatment with lysing agents. A preferred commercial selective cell lysis agent for the present invention is ZAP-OGLOBIN® manufactured by Coulter Diagnostics, a division of Coulter Electronics, Inc. (Hialeah, Fla., U.S.A.). When ZAP-OGLOBIN® is used, it is preferred that it is diluted in ISOTON®II, a diluent manufactured by Coulter Diagnostics and described in U.S. Pat. No. 3,962,125, hereby incorporated by reference.

Cell Concentration. The major concern with red blood cell lysis is the release of heme and related compounds which inhibit Taq polymerase. *PCR Technology*, H. A. Erlich (ed.) Stockton Press (1989) p. 33. It can be estimated that the concentration of heme in hemolyzed whole blood is approximately 10mM assuming normal hemoglobin concentration in whole blood is 15 g/100 ml. Hematology, 2nd ed., W. J. Williams et al. (ed.) McGraw-Hill, N.Y. (1977). This is far above the reported inhibitory concentration of 0.8 $\mu$M.

Following the selective lysis step, a process step is performed that involves concentration of the cells. As noted above, concentration is defined broadly and may result from a wide variety of techniques, including filtration, agglutination, centrifugation, immobilization, and/or fluid evaporation. In a preferred embodiment, the concentration step simultaneously removes polymerase inhibitors such as heme and related compounds.

In one embodiment, centrifugation at 250 g for 10 minutes is performed, pelleting predominantly white blood cells and leaving the majority of platelets in the supernatant. In another embodiment, microfuging for as short as one minute is performed, pelleting both white blood cells and platelets. The presence of platelets is found not to impact subsequent steps of the whole blood processing method of the present invention. The advantages of this white blood cell concentration step are: (1) centrifugation is quick (compare, for example, gradient centrifugation); (2) stored blood can be used; 3) cells are in pellet form and thus easier to collect than cells supported at a gradient interface; and, (4) essentially complete (quantitative) recovery of white blood cells is possible (i.e. high yield).

The centrifugation step to pellet white blood cells may be varied depending on which version (a or b, see FIG. 1) of Mode I is utilized. Where version a is utilized, an inhibitor treatment step is employed. Since an inhibitor treatment step will avoid problems with residual potential polymerase inhibitors, the prior centrifugation step can be performed with only one centrifugation. With one centrifugation, the majority of the heme is removed with the supernatant and the remaining heme can be successfully treated in the later step. On the other hand, where no inhibitor treatment step is employed, it has been determined that two washings of the cell pellet are necessary for the residual heme to be at non-inhibitory levels.

In another embodiment, filters are used for cell concentration. Indeed, the present invention demonstrates the efficacy of some filters - but not others - to separate white blood cells from a small volume (less than 1 ml and preferably less than 0.1 ml) of whole blood that has been subjected to selective lysis.

Non-Selective Cell Lysis. Following concentration, the cells can then be non-selectively lysed. The preferred non-selective lysing agent is protease K. Protease K is a proteolytic enzyme from *Tritirachium album*. It is particularly useful in the present invention because it has no significant DNAse activity and, therefore, does not render nucleic acid unamplifiable. It is also attractive because it is inexpensive and commercially available (e.g. Sigma, St. Louis, Mo., U.S.A., catalogue No. p4914 "Proteinase K"). Various treatment conditions using protease K have been found useful. It is preferred that high concentration of protease K (e.g. 1.5-2.5 mg/ml) be used for short (5-10 minutes) incubation periods to completely degrade cellular as well as plasma protein and expose cellular nucleic acid for amplification. When lower protease K concentrations (e.g. 0.5 mg/ml) are used, longer incubation periods (30-60 minutes) are required to achieve the same effect. So that amplification may be carried out, it is preferred that protease K is inactivated. inactivation may be achieved thermally (preferred) or chemically. If chemical, the preferred inactivation is by the addition of a chelating agent, such as ethylenediaminetetraacetic acid (EDTA). EDTA removes $Ca^{+2}$ ions required for protease K activity. See Bajorath et al., Nature 337:481 (1989).

Where bacterial cells are believed to be contaminating the white cell preparation, it may be desirable to lyse the bacterial cells prior to, together with, or after lysis of the white cells. This may depend on whether amplification of bacterial sequences is intended. Lysis of bacterial cells can be accomplished enzymatically or chemically. If accomplished enzymatically, it is contemplated that lysozyme or mutanolysin is used, both of which are commercially available (e.g. Sigma). Lysozyme (also called "muramidase") is a single polypeptide of 129 amino acids which dissolves bacterial cell wall mucopolysaccharides by hydrolyis. Mutanolysin apparently exists in two major molecular forms, a 22,000 MW and an 11,000 MW form. Both forms have pronounced lytic activity on a vast array of bacteria.

Following non-selective lysis, Mode I may or may not have another step before amplification (see FIG. 1). In one version ("b"), the method proceeds directly to amplification. In another ("a"), the method proceeds to an inhibitor treatment step.

Inhibitor Treatment. As noted above, by "inhibitor treatment" it is meant that a process is carried out to treat some potential, residual polymerase inhibitors such as heme and its related compounds. The process may be chemical, biochemical, photochemical, immunological, or enzymatic, or any combination thereof. In each case, the inhibitor treatment of the present invention does not render the nucleic acid unamplifiable, i.e. the treatment does not impair subsequent amplification.

Chemical. In one embodiment, a chemical process is utilized that is directed at the chemical breakdown of potential inhibitors by disrupting heme-type inhibitors by either oxidation or reduction so as to change their geometry or coordination chemistry, preventing interaction with polymerase. Where reduction chemistry is used, the preferred reducing agent is a hydride, such as sodium borohydride. Where oxidation is used, the preferred oxidizing agent is ascorbate.

Biochemical. In one embodiment, a biochemical process is utilized wherein a reagent is introduced that will interfere with the inhibition of polymerase by inhibitors present in whole blood. In one embodiment, such "interfering reagents" comprise compounds selected from the group consisting of porphyrin-binding compounds. The present invention contemplates that porphorin-binding compounds include heme-binding compounds, such as the 93,000 molecular weight, heme-binding protein from rabbit serum. See Tsutsui and Mueller, J. Biol. Chem. 257, 3925-3931, 1982). This heme-binding protein appears to be unique to rabbits; no analogous proteins have been found in other species tested thus far (human, calf and rat).

In one embodiment, interfering reagents comprise compounds selected from the group consisting of globin, serum albumin, and transferrin. The preferred compounds are serum albumin and transferrin. Where serum albumin or transferrin are used to treat polymerase inhibitors, the present invention provides cofactors to be used in conjunction. Cofactors are characterized in that they are typically mono- or divalent anions. In one embodiment, the cofactor is selected from the group consisting of bicarbonate ion, azide ion, thiocyanate ion, cyanate ion, oxalate ion, malonate ion, glycinate ion and thioglycolate ion. The cofactor normally is supplied as a salt (e.g. sodium bicarbonate). The preferred cofactors when transferrin is used are bicarbonate ion, thiocyanate ion, cyanate ion, glycinate ion and thioglycolate ion.

Bovine serum albumin (BSA) has been used in PCR to overcome an inhibitory activity of unknown origin that is present in many extracts of ancient DNA (i.e.

museum specimens and archaeological finds). See *PCR Protocols: A Guide To Methods and Applications*, Innis, M.A. et al. eds., pp. 159–166 (1990). Inhibition of polymerase by heme-type compounds has not been shown to be overcome with BSA. The present invention describes this for the first time and demonstrates a cofactor requirement.

Transferrin, a blood serum component, is an iron transport protein. Its molecular weight was reported to be between 70,000–90,000 depending on the species of origin. Metal ion binding of transferrin is a well studied phenomena. For example, in the presence of an anion (such as $HCO_3^-$), transferrin has the capacity to take up 2 iron atoms per molecule. There are, however, no previous reports regarding the ability of transferrin to overcome the inhibition of polymerases by heme.

While not limited to any mechanisms, it would appear that the herein described ability of transferrin to overcome the inhibition of polymerases by heme-type compounds is not mediated by metal ion binding. First there is the question of stoichiometry: the molar ratio of transferrin to heme at which transferrin is most effective in binding heme is <0.27. This is lower than that expected from the molar ratio of transferrin to iron binding ratio of 0.5. Second, there is the question of the central metal ion: the central metal iron was found not to be required for the transferrin-mediated phenomenon of the present invention. This is evident from the demonstration (described herein) that transferrin is able to overcome the inhibition of polymerases by protoporphyrin, a heme molecule free of the central metal iron.

Photochemical. The present invention also contemplates a photochemical treatment to eliminate inhibition of polymerase by inhibitors. A preferred photochemical treatment comprises exposure of potential inhibitors to ultraviolet radiation. Particular types of ultraviolet radiation are herein described in terms of wavelength. Wavelength is herein described in terms of nanometers ("nm"; $10^{-9}$ meters). For purposes herein, ultraviolet radiation extends from approximately 180 nm to 400 nm. When a radiation source does not emit radiation below a particular wavelength (e.g. 300 nm), it is said to have a "cutoff" at that wavelength (e.g. "a wavelength cutoff at 300 nanometers").

When ultraviolet radiation is herein described in terms of irradiance, it is expressed in terms of intensity flux (milliwatts per square centimeter or "mW cm$^{-2}$"). "Output" is herein defined to encompass both the emission of radiation (yes or no; on or off) as well as the level of irradiance.

A preferred source of ultraviolet radiation is a fluorescent source. Fluorescence is a special case of luminescence. Luminescence involves the absorption of electromagnetic radiation by a substance and the conversion of the energy into radiation of a different wavelength. With fluorescence, the substance that is excited by the electromagnetic radiation returns to its ground state by emitting a quantum of electromagnetic radiation. While fluorescent sources have heretofore been thought to be of too low intensity to be useful for photochemical treatment, in one embodiment the present invention employs fluorescent sources to achieve photochemical treatment of polymerase inhibitors. A preferred fluorescent source is a device ("HRI-100") sold commercially by HRI Research Inc. (Berkeley, Calif., USA) and ULTRA-LUM, INC. (Carson, Calif., USA).

Immunological. The present invention also contemplates an immunological treatment to eliminate inhibition of polymerase by inhibitors. Where specific inhibitors are sought to be treated immunologically, the present invention contemplates the use of antibodies directed at such inhibitors. In one embodiment, antibodies are raised by immunization with specific inhibitors. The inhibitors may be obtained from cells disrupted by treatments which include sonic disruption, osmotic change or use of agents such organic solvents, detergents, enzymes and the like.

Furthermore, immunological equivalents of the inhibitors (e.g. protein fragments) may be used to facilitate the production of antibodies. Additionally, a mixture of inhibitors may be used to facilitate the production of antibodies.

The antibodies may be monoclonal or polyclonal. It is within the scope of this invention to include any second antibodies (monoclonal or polyclonal) directed to the first antibodies discussed above. The methods of obtaining both types are well known in the art. Polyclonal sera are relatively easily prepared by injection of a suitable laboratory animal with an effective amount of the inhibitor or antigenic parts thereof, collecting serum from the animal, and isolating specific sera by any of the known immunoadsorbent techniques.

The preparation of hybridoma cell lines for monoclonal antibody production derived by fusing an immortal cell line and lymphocytes sensitized against the immunogenic preparation can be done by techniques which are well known to those who are skilled in the art. (See, for example Douillard and Hoffman, Basic Facts about Hybridomas, in *Compendium of Immunology* Vol II, ed. by Schwartz, 1981; Kohler and Milstein, *Nature* 256: 495–499, 1975; *European Journal of Immunology* 6: 511–519, 1976).

Unlike preparation of polyolonal sera, the choice of animal is dependent on the availability of appropriate immortal lines capable of fusing with lymphocytes. Mouse and rat have been the animals of choice in hybridoma technology and are preferably used.

The utilization of an antibody produced in the above-described manner may be accomplished in a number of ways such as providing antibody on a solid support and passing the products of the non-selective lysis step over the solid support. On the other hand, the antibody may be introduced in solution to the products of the non-selective lysis step.

Enzymatic. The present invention also contemplates an enzymatic treatment to eliminate inhibition of polymerase by inhibitors. For example, the present invention contemplates the use of heme oxygenase to treat heme-type inhibitors. Heme oxygenase is the enzyme associated with the first step of heme catabolism in eukaryotes. Degradation of heme to bile pigments is mediated by heme oxygenase. Molecular oxygen (as well as NADPH) is required for this oxidation which results in attack at the alpha meso carbon bridge of the heme, releasing CO and forming biliverdin. See Schacter, Sem. in Hem. 25:349 (1988). Thereafter, biliverdin may be converted to bilirubin by the enzyme biliverdin reductase.

Combination. The present invention also contemplates an inhibitor treatment step that involves a combination of the above-named process steps. For example, the present invention contemplates the chemical oxidation of heme-type inhibitors followed by photochemical destruction of the products of chemical oxidation. In another embodiment, the present invention contemplates the enzymatic degradation of heme-type inhibitors followed by the photochemical destruction of the products of enzymatic degradation. In still another embodiment, the present invention contemplates an inhibitor treatment step that involves a simultaneous use of two or more of the above-named process steps (e.g. chemical reduction in the presence of particular ultraviolet wavelengths).

Mode II

Cell Concentration. As noted above, "concentration" is defined broadly and may result from a wide variety of techniques, including immobilization and/or fluid evaporation. In one embodiment, the present invention contemplates immobilizing whole blood in low melting agarose. In this embodiment, the blood sample is placed in warm (melted) agarose which is then congealed at room temperature. The agarose can thereafter be melted for subsequent processing steps (see below).

In another embodiment, whole blood is immobilized on an absorptive support and dried. In this regard, the present invention demonstrates the efficacy of some filters—but not others—to immobilize blood cells from a small volume (less than 1 ml and preferably less than 0.1 ml) of whole blood.

In another embodiment, white blood cells are immobilized on a solid support while red blood cells are not. With respect to the latter, various filters have been used and proven effective in immobilizing only white blood cells.

Since platelets are much smaller than either red blood cells or white blood cells, and red blood cells have a different shape from white blood cells, pore sizes can be chosen to allow passage of platelets and red blood cells while facilitating adhesion of white blood cells to the filter materials. Different pore sizes and filtration flow rates have been found useful in the concentration step of the present invention.

Non-Selective Cell Lysis. As noted for Mode I, the preferred non-selective lysing agent for Mode II is protease K. Other non-selective lysis approaches, however, are also contemplated, including lysis by heating whole blood. Where whole blood has been previously immobilized by adding to a filter and drying, the present invention contemplates non-selective cell lysis in the presence of the filter. In one embodiment, the filter is selected that will subsequently dissolve during the non-selective lysis step (e.g. with protease K, a protein filter is selected). In another embodiment, the filter disc is impregnated with the lysing agent prior to immobilization of whole blood. In this way, the concentration step and the lysis step of Mode II are performed simultaneously.

Inhibitor Treatment. The inhibitor treatment for Mode II is also contemplated to be chemical, biochemical, photochemical, immunological, or enzymatic, or any combination thereof. Where whole blood has been previously immobilized by adding to a filter and drying, the present invention contemplates inhibitor treatment in the presence of the filter. In one embodiment, the filter is selected that will be tolerated by the inhibitor treatment (e.g. with a chemical inhibitor treatment, an inert filter is selected). In another embodiment, a second filter disc (impregnated with a inhibitor treatment agent such as interfering reagent) is used along with the filter disc having the immobilized whole blood. In this way, the concentration step and the lysis step of Mode II are performed simultaneously on one disc and the inhibitor treatment is performed thereafter by the introduction of a second disc.

Mode III

Non-Selective Cell Lysis. As noted for Mode I, the preferred non-selective lysing agent for Mode II is protease K. Other non-selective lysis approaches, however, are also contemplated, including lysis by heating whole blood.

Inhibitor Treatment. The inhibitor treatment for Mode II is also contemplated to be chemical, biochemical, photochemical, immunological, or enzymatic, or any combination thereof.

From the above, it is clear that the present invention provides a useful, and yet flexible, approach to preparing nucleic acid sequences. Which mode is most appropriate depends on the concentration of the sequence of interest. The concentration of the sequence of interest is determined by the sample size and copy number. For low copy number systems, one typically needs a larger sample size in order to be sure the sequence of interest is present in the sample. Large sample sizes, however, have more inhibitor. Furthermore, large samples are not readily amenable to amplification because of the expense of large sample amplification as well as the inhibiting impact of vary large amounts of nucleic acid on most amplification techniques.

The above considerations are best understood by example. The low copy situation of virus infection is a good case in point. Since the number of HIV infected T4 cells can be as low as one out of every 10,000 and only 14% of the total white blood cell population is T4, for each HIV PCR beginning with 40 infected T4 cells, a minimum of 300-600 $\mu$l of normal whole blood will be required. A larger volume may be needed for HIV patients due to depletion of their T4 cells. However, since the PCR is normally carried out in 100 ul, a volume reduction step, which allows concentrations of white blood cells, may be necessary to avoid the expense of large amounts of enzyme.

One potential problem of the cell concentration steps is that the final amount of DNA obtained by the procedure may be to high for the PCR to efficiently proceed. It has been shown that the amount of DNA present in 0.5 ml of normal whole blood is difficult or impossible to amplify all at once by the PCR. The occurrence of DNA dependent PCR inhibition is probably due to an excess of mispriming sites (relative to enzyme molecules), which form unproductive ternary complexes with the polymerase. This results in the accumulation of a large number of linearly or exponentially amplified non-target sequences. Since the specificity of the amplification is lost as the amount of non-target DNA is increasing, the exponential accumulation of the target sequence of interest does not occur to any significant degree.

EXPERIMENTAL

In the experimental disclosure which follows, all weights are given in grams (g), milligrams (mg) or micrograms ($\mu$g), all lengths are given as centimeters (cm), millimeters (mm), micrometers ($\mu$m) or nanometers (nm), all pressures are given as pounds per square inch (psi), all temperatures are given as degrees Centigrade (°C.), all concentrations are given as percent by weight (% or percent), equivalents (eq), Normal (N), molar (M), millimolar (mM) or micromolar ($\mu$M), all quantities are given as moles (mol), millimoles (mmol), micromoles (μmol) or nanomoles (nmol) and all volumes are given as liters (l), milliliters (ml), or microliters (μl) unless otherwise indicated.

In addition, the following abbreviations have the indicated meanings: MW (molecular weight); OD (optical density); EDTA (ethylenediaminetetraacetic acid); TE buffer (buffer: 10 mM Tris/1 mM EDTA, pH 7.5); TBE buffer (Tris-Borate-EDTA); TAE buffer (Tris-Acetate-EDTA); Taq buffer (50 mM KCl, 2.5 mM MgCl$_2$, 10 mM Tris, pH 8.5, 200 μg/ml gelatin); PAGE (polyacrylamide gel electrophoresis); SDS-PAGE (sodium dodecyl sulfate-polyacrylamide gel electrophoresis); V (volts); W (watts); mA (milliamps); bp (base pair); kb (kilobase pairs); Ci (Curies); μCi (microcuries) and CPM (counts per minute).

Generally, PCR was carried out using 175–200 μM dNTPs (deoxyribonucleoside 5'-triphosphates) and 0.5 to 1.0 μM primers. 5 Units/ 100 μl of Taq polymerase was used. PCR reactions were overlaid with 30–100 μl light mineral oil. A typical PCR cycle for HIV amplification using a Perkin-Elmer Cetus DNA Thermal Cycler (Part No. N8010150) was: denaturation at 95° C. for 30 seconds; annealing at 55° C. for 30 seconds; and extension at 72° C. for 1 minute. PCR cycles were normally carried out in this manner for 35 cycles followed by 7 minutes at 72° C.

In some instances below, amplification of human histocompatibility (HLA) Class II genes was performed using primer pair GH26/GH27 and human placental DNA to produce a 242-mer product. The sequences of these primers are:

| | |
|---|---|
| GH26 | 5'-GTGCTGCAGGTGTAAACTTGTACCAG-3' |
| GH27 | 5'-CACGGATCCGGTAGCAGCGGTAGAGTTG-3' |

These primers and other primers are described in *PCR Protocols: A Guide To Methods and Applications*, Innis, M.A. et al. eds., pp. 261–271 (1990)). The sequence of the 242-mer product is:

| | |
|---|---|
| 242-mer | 5'-GTGCTGCAGG TGTAAACTTG TACCAGTTTT ACGGTCCCTC TGGCCAGTAC ACCCATGAAT TTGATGGAGA TGAGGAGTTC TACGTGGACC TGGACAGGAA GGAGACTGCC TGGCGGTGGC CTGAGTTCAG CAAATTTGGA GGTTTTGACC CGCAGGGTGC ACTGAGAAAC ATGGCTGTGG CAAAACACAA CTTGAACATC ATGATTAAAC GCTACAACTC TACCGCTGCT ACCGGATCCG TG-3' |

In other cases, amplification of HIV sequences was performed using primer pair SK-38/SK-39 and 115-mer as target to produce a 115-mer product. The sequences of these primers are:

| | |
|---|---|
| SK38 | 5'-ATAATCCACCTATCCCAGTAGGAGAAAT |
| SK39 | 5'-TTTGGTCCTTGTCTTATGTCCAGAATGC |

The sequence of the 115-mer product is:

| | |
|---|---|
| 115-mer | 5'-ATAATCCACC TATCCCAGTA GGAGAAATTT ATAAAAGATG GATAATCCTG GGATTAAATA AAATAGTAAG AATGTATAGC CCTACCAGCA TTCTGGACAT AAGACAAGGA CCAAA-'3 |

In one case, amplification of globin sequences was performed using primer pair KM-29/HRI-12. These primers give a 174 bp product within the human beta globin gene. The sequences of these primers are:

| | |
|---|---|
| KM-29 | 5'-GGTTGGCCAATCTACTCCCAGG-3' |
| HRI-12 | 5'-GGCAGTAACGGCAGACTACT-3' |

Where agarose gel electrophoresis was used, the PCR products were fractionated by electrophoresis through a 3% Nusieve/1 % agarose gel in TBE buffer. Electrophoresis was typically carried out in a constant voltage of 8–10 V/cm. Following agarose gel electrophoresis, individual bands were, in most cases, visualized by ethidium bromide staining. This involved staining the agarose gel with 1 μg/ml ethidium bromide in TBE for 30 minutes followed by destaining the agarose gel with TBE for 30 minutes.

Where polyacrylamide gel electrophoresis (PAGE) was used, two types of gels were used, denaturing and native. Denaturing (7 or 8M urea) polyacrylamide gels (28 cm×35 cm×0.4 mm) were poured and preelectrophoresed for 30 to 60 minutes at 2000 Volts, 50 Watts, 25 milliamps. 12% gels were used for oligonucleotides between 40 and 200 base pairs in length; 8% gels were used for longer sequences. Depending on the length of DNA to be analyzed, samples were loaded in either 8M urea, containing 0.025% tracking dyes (bromphenol blue and xylene cyanol), or in 80% formamide, 10% glycerol, 0.025% tracking dyes, then electrophoresed for 2–4 hours at 2000 Volts, 50 Watts, 25 milliamps. Following PAGE, individual bands were, in most cases, visualized by autoradiography. Autoradiography involved exposure overnight at −70° C. to Kodak XAR-5 films with an intensifying screen.

In order to visualize with autoradiography, PCR products were internally radiolabelled. This simply involved adding 2 μCi of α-$^{32}$P-dCTP (3000 Ci/mmole, NEN Research Products, Boston Mass., U.S.A.) to each PCR reaction. The internally-radiolabelled PCR products are directly fractionated by this denaturing PAGE without prior treatment.

Native polyacrylamide gels were poured similarly to the denaturing gel with the urea left out. No pre-electrophoresis was necessary. Samples were loaded in 10 mM Tris, 10 mM EDTA, 0.1% SDS, 10% glycol, 0.025% tracking dyes. Following PAGE, analysis was carried out as described above for denaturing gels.

SDS-PAGE was used to fractionate protein molecules. Generally, the gel used was 10% polyacrylamide in 0.375 M Tris pH 8.8 and 0.1% SDS. The stacking gel was 5% polyacrylamide in 0.125 M Tris pH 6.8 and 0.2% SDS. Running buffer was 0.025M Tris pH 8.3, 0.192M glycine and 0.1% SDS. Protein samples were dissolved in 0.0625 M Tris pH 6.8, 2% SDS, 5% β-mercaptoethanol containing 10% glycerol and tracking dye (BPB) and heated to 100° C. for 2 minutes before loading. After electrophoresis, the protein bands were visualized after staining with 0.1% coomassie blue (Sigma) in 50% Methanol and 10% trichloroacetic acid for 1 hour followed by destaining in 5% methanol and 7% acetic acid.

Ouchterlony immunodiffusion gels were used. See generally, E. A. Kabat, *Structural Concepts in Immunology and Immunochemistry* (Holt, Rinehart and Winston, N.Y. 1968). An agarose solution is poured into a standard petri dish on a microscope slide. After the gel hardens, a center well and surrounding wells are punched out and the agarose plugs removed. A solution of antibody is placed in the center well and solutions of the relevant test samples are placed separately in the surrounding wells. The petri dish is placed at 4° C. overnight and then inspected visually for precipitin lines.

Photochemistry was performed using a device ("HRI-100") sold commercially by HRI Research Inc. (Berkeley, Calif., USA) and ULTRA-LUM, INC. (Carson, Calif., USA).

In some cases, amplified products were visualized by Oligonucleotide Hybridization (OH) analysis. PCR products were mixed with radiolabeled probe in 10 mM EDTA, 15 mM NaCl, denatured for 5 minutes at 95° C., followed by an annealing step at 55° C. for 15 minutes. The hybrids were separated from unincorporated probe by PAGE with a native gel.

Probes were end-labeled with $\gamma$-$^{32}$P-ATP by T$_4$ polynucleotide kinase. Typically, 0.2 $\mu$g of an oligonucleotide probe was incubated with 20 $\mu$Ci $\gamma$-$^{32}$P-ATP (6000 Ci/mmole, NEN Research Products, Boston Mass., U.S.A.) and 20 units of T$_4$ polynucleotide Kinase (New England BioLab) at 37° C. for one hour. After stopping the reaction with 25 mM EDTA, the labeled probe was separated from unincorporated $\gamma$-$^{32}$P-ATP by a spin column chromatography. A mini-sephadex G-50 column (1 ml) was packed by centrifugation (2 min, 1,800 rpm in a table top ntrifuge) in a 1 ml disposable syringe in TE. The T$_4$ Kinase reaction products were loaded over the top of the column and centrifuged again at 1,800 rpm for 2 minutes. The labeled probe is collected in the exclusion volume.

In some examples, clinical samples were supplied by the California Department of Public Health (CDPH) and used to validate the compounds and methods of the present invention. Each of the high risk patient samples were evaluated by the CDPH for antibody to HIV ("serotested") by ELISA assay using the Organon Teknika ELISA kit. This kit contains multiple antigens with predominantly p24. Each sample was tested twice.

The ELISA results were thereafter confirmed by an immunofluorescence assay (IFA) performed at the CDPH. For this test, HIV infected H9 cells expressing HIV antigens were fixed on microscope slides. A drop of serum from the clinical sample was added to the fixed cells. After incubation, unbound serum constituents were washed away. A second antibody specific to human immunoglobin conjugated with fluorescein isothiocyanate (FITC) was added. The bond serum antibody to HIV was then visualized under a fluorescent microscope.

In case there is a disagreement between the ELISA results and the IFA results, then both the Western Blott and Radioimmunoprecipitation Assay (RIPA) were used to determine if a sample is indeed positive.

The following examples are provided in order to demonstrate and further illuminate certain aspects of the practice of the invention.

EXAMPLE 1

Figure 2B:
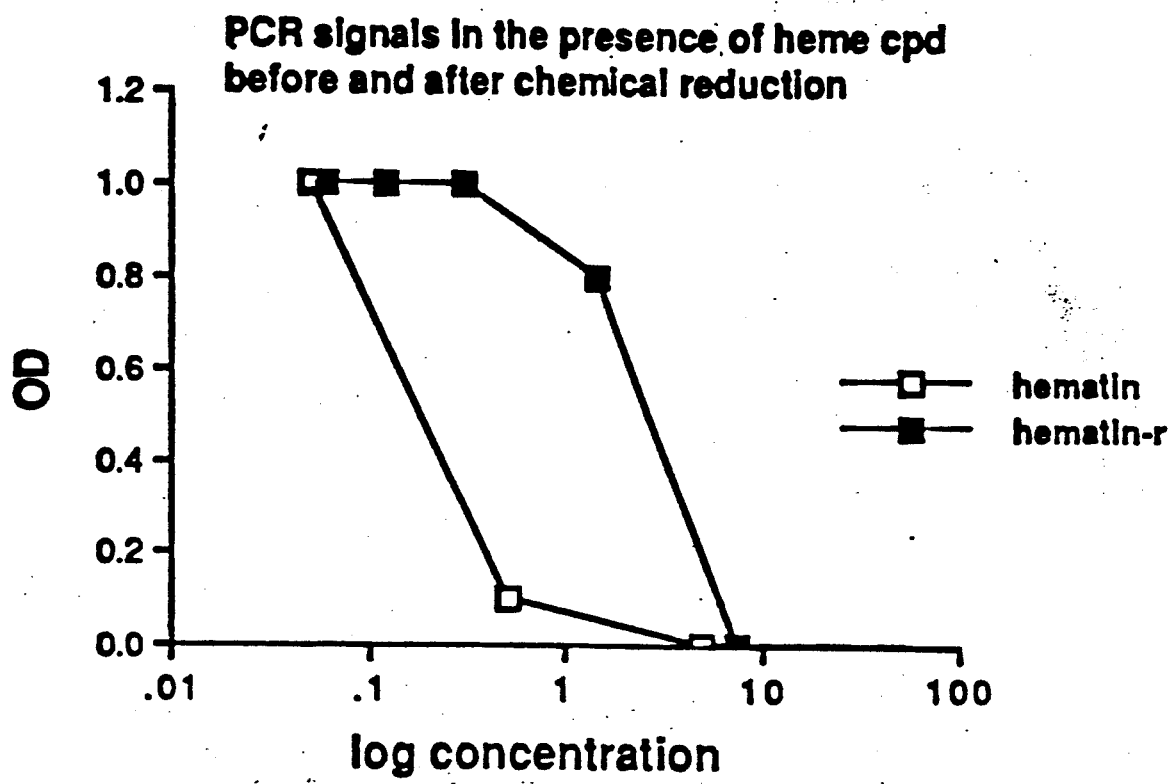
FIG. 2B is a graph showing quantitative changes in PCR signal following chemical reduction of hematin.

In this example, the effect of chemical treatment of hematin on inhibition of amplification is demonstrated. The chemical reaction was performed as follows. Two aliquots (30 mg/aliquot) of sodium borohydride (NaBH$_4$) were added at ten minute intervals to 1 ml of 200 $\mu$M hematin (Sigma) in 1M Tris (pH 8.0) under argon in the dark. The pH was adjusted to 6.0 between additions. At the end of the reaction (20 minutes) the pH was adjusted to 1.0 and then neutralized to pH 7.0. Six aliquots (5 $\mu$l) of the product of the reaction corresponding to different amounts of reacted hematin (37.5 $\mu$M, 7.5 $\mu$M, 1.5 $\mu$M, 0.3 $\mu$M, 0.06 $\mu$M, 0.012 $\mu$M) were added to standard (20 $\mu$l) PCR reactions in different tubes using the SK38/39 system (see above). Three standard control reactions were run in separate tubes: i) a no nucleic acid target control, ii) a no primer control, and iii) a positive control (no hematin). In addition, unreacted hematin was added to four different tubes in different amounts (50 $\mu$M, 5 $\mu$M, 0.5 $\mu$M, and 0.05 $\mu$M). PCR was carried out for 30 cycles. The PCR products were thereafter electrophoresed (agarose) and visualized with ethidium bromide staining (FIG. 2A, lanes 1-13). The three above-named control reactions were electrophoresed in lanes 1, 2 and 3, respectively. As expected, no product is visible in lanes 1 and 2 (negative controls), while a strong product band corresponding to the expected 115-mer is apparent in lane 3 (positive control). The unreacted hematin tubes (lanes 4-7) show no product until hematin is present at a very low concentration (0.05 $\mu$M, lane 7), at which point product is evident. On the other hand, product is visible in some of the lanes (lanes 10-13) representing reactions where treated hematin was added (lanes 8-13). Indeed, product is evident where 1.5 $\mu$M reacted hematin or less was present. FIG. 2B shows a more quantitative analysis of the reaction based on the best visual estimation of the band intensity. A score (i.e. % maximum intensity of a positve control) was given to each band. An OD unit of 1.0 corresponds to 100% of maximum intensity. After examination of a plot of the estimated OD units to the concentration of hematin (expressed in the log scale) in these PCR reactions, it is clear that approximately a thirty-fold concentration difference was achieved (reacted to unreacted).

EXAMPLE 2

In this example, the effect of photochemical treatment of biliverdin on inhibition of amplification is demonstrated. The photochemical reaction was performed as follows. Stock biliverdin (Sigma, 5 mM) was diluted in solution (50 mM Tris pH 7.8) to a final concentration of 200 $\mu$M. Two aliquots (300 $\mu$l) were then made. One aliquot was left unreacted. The other aliquot was exposed to ultraviolet radiation from an HRI-100 for 16 hours using the industry standard, F8T5BL hot cathode dual bipin lamps. Thereafter, both the unirradiated and irradiated material were added (5 $\mu$l) to standard (20 $\mu$l) PCR reactions in different tubes using the SK38/39 system (see above) and 10$^9$ copies of 115-mer target. Three standard control reactions were run in separate tubes: i) a no nucleic acid target control, ii) a positive control (no biliverdin), and iii) a no Taq control. PCR was carried out for thirty (30) cycles. The PCR products were thereafter electrophoresed (agarose) and visualized with ethidium bromide staining (FIG. 3A, lanes 1-5). The three above-named control reactions were electrophoresed in lanes 1, 2 and 3, respectively. As expected, no product is visible in lanes 1 and 3 (negative controls), while a strong product band corresponding to the expected 115-mer is apparent in lane 2 (positive control). The unirradiated biliverdin tube (lanes 4) shows no product, i.e. PCR is completely inhibited. On the other hand, product is visible in the lane (lane 5) representing the reaction where photochemically treated (16 hrs) biliverdin was added.

Figure 3B:
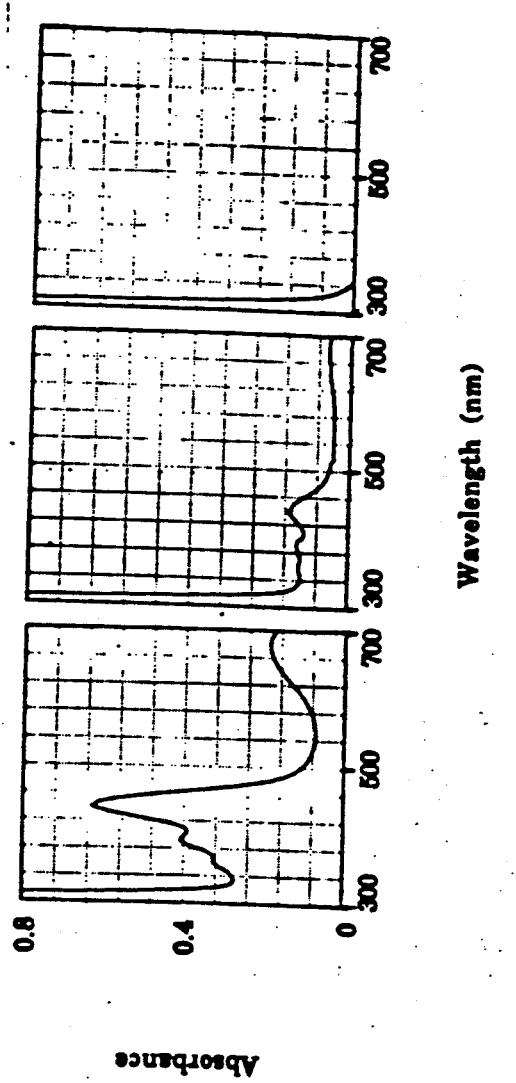

A spectroscopic analysis of the photochemical treatment is shown in FIG. 3B. In this case 0.5 ml of untreated biliverdin in solution (diluted in 50 mM Tris pH 7.8 to a final concentration corresponding to $A_{peak}=0.7$) was scanned using a Beckman Spectrophotometer Model DU-50 between 300 and 700 nm. Photochemically treated (1.5 hours and 16 hours of irradiation) biliverdin was similarly diluted and scanned. The results are shown in FIG. 3B. The untreated biliverdin shows a strong absorbance peak at approximately 450 nm. With just 1.5 hours of irradiation, this peak is very weak; with 16 hours, it is eliminated completely. This corresponds to lane 5 in FIG. 3A where no PCR inhibition was observed.

EXAMPLE 3

Figure 4A:
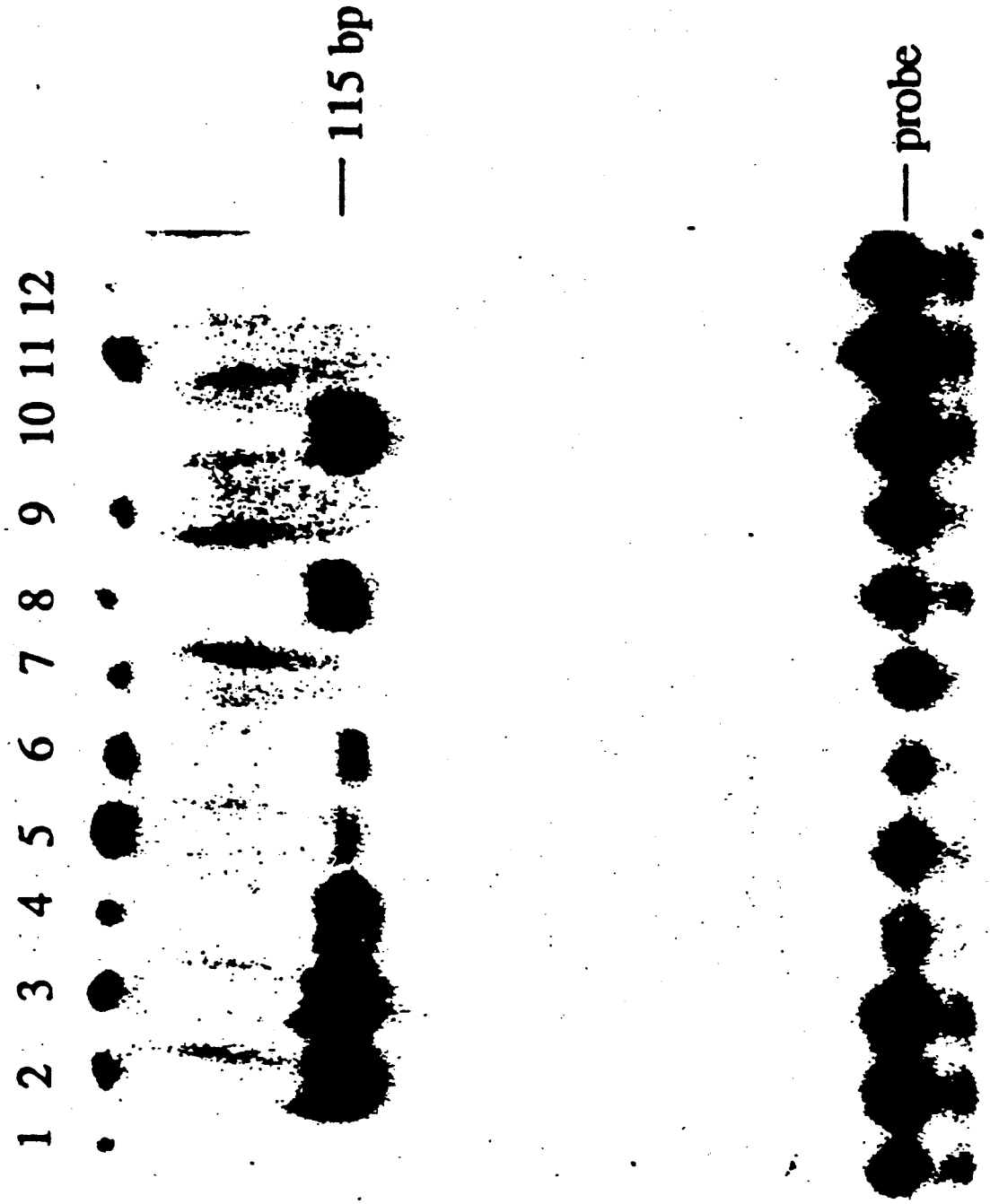
FIG. 4A is a photograph of an autoradiograph of electrophoresed, PCR-amplified, internally-radiolabelled, HIV sequences following photochemical treatment of bilirubin.

In this example, the effect of photochemical treatment of bilirubin on inhibition of amplification is demonstrated. The photochemical reaction was performed as follows. Stock bilirubin (Sigma, 5 mM) was diluted in solution (50 mM Tris pH 7.8)) to final concentrations of 400 µM, 800 µM and 2 mM. Two aliquots (300 µl) at each concentration were then made. One aliquot of each concentration was left unreacted. The other aliquot was exposed to ultraviolet radiation from an HRI-100 for 0–4 hours using the industry standard, F8T5BL hot cathode dual bipin lamps. Thereafter, both the unirradiated and irradiated material were added (5 µl) to standard (20 µl) PCR reactions in different tubes using the SK38/39 system (see above) and $10^{11}$ copies of 115-mer target. Six standard control reactions were run in separate tubes: i) a no nucleic acid target control, and ii-vi) five positive control (no bilirubin), each starting with a different copy number ($10^{11}$, $10^9$, $10^7$, $10^5$, and $10^3$). PCR was carried out for thirty (30) cycles in the presence of $\alpha$-$^{32}$P-dCTP (NEN Research Products, Boston Mass., U.S.A.). The PCR products were thereafter electrophoresed (denaturing PAGE), and visualized by autoradiography (FIG. 4A, lanes 1–12). The six above-named control reactions were electrophoresed in lanes 1–6, respectively. As expected, no product is visible in lane 1, while a product band corresponding to the expected 115-mer is apparent in lanes 2–6. Where unreacted bilirubin was used (lanes 7, 9 and 11) there is no product evident, i.e. PCR is completely inhibited. On the other hand, product is visible in the lanes (lane 8, 400 µM bilirubin, 2.5 hrs; and lane 10, 800 µM bilirubin, 3.5 hrs) representing the reaction where photochemically treated bilirubin was added in concentrations less than 800 µM. Product is not visible in the lane (lane 12, 2 mM bilirubin, 4 hrs) representing the reaction where photochemically treated bilirubin was added in very high concentration (2 mM).

Figure 4B:
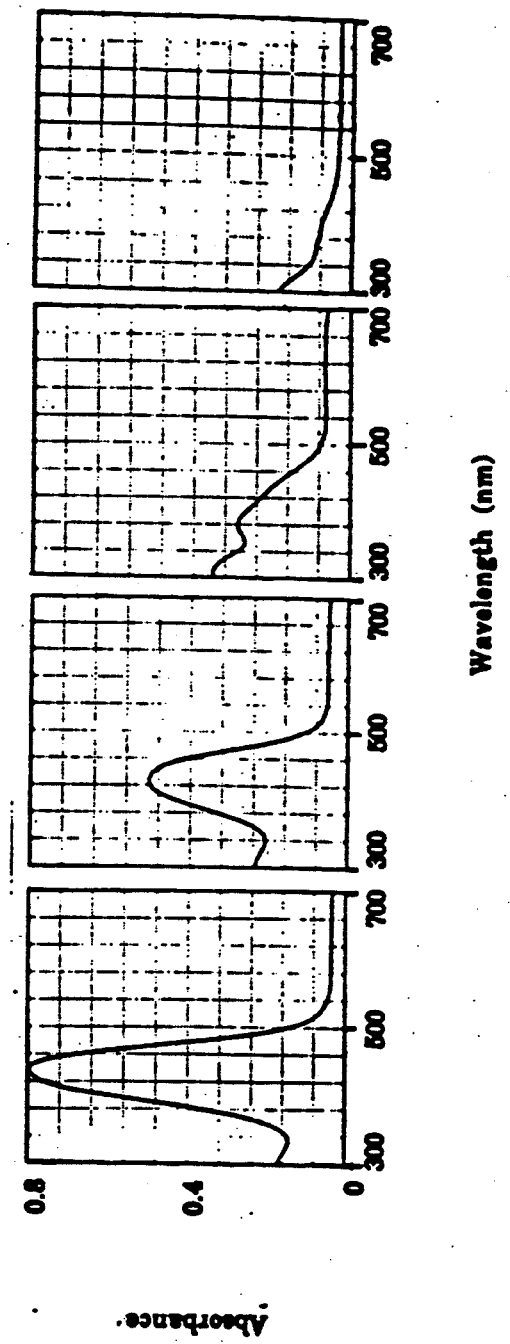

A spectroscopic analysis of the photochemical treatment is shown in FIG. 4B. In this case 0.5 ml of untreated bilirubin in solution (diluted in 50mM Tris, pH 7.8 to a final concentration corresponding to $A_{Peak}=0.8$) was scanned using a Beckman Spectrophotometer Model DU-50 between 300 and 700 nm. Photochemically treated (20 minutes, 60 minutes and 2.5 hours of irradiation) bilirubin was similarly diluted and scanned. The results are shown in FIG. 4B. The untreated bilirubin shows a strong absorbance peak at approximately 450 nm. With just 20 minutes of irradiation, this peak is reduced; with just 60 minutes of irradiation, this peak is weak; with 2.5 hours, it is eliminated. The 2.5 hour treatment corresponds to lane 8 in FIG. 4A where no PCR inhibition was observed.

EXAMPLE 4

Figure 5:
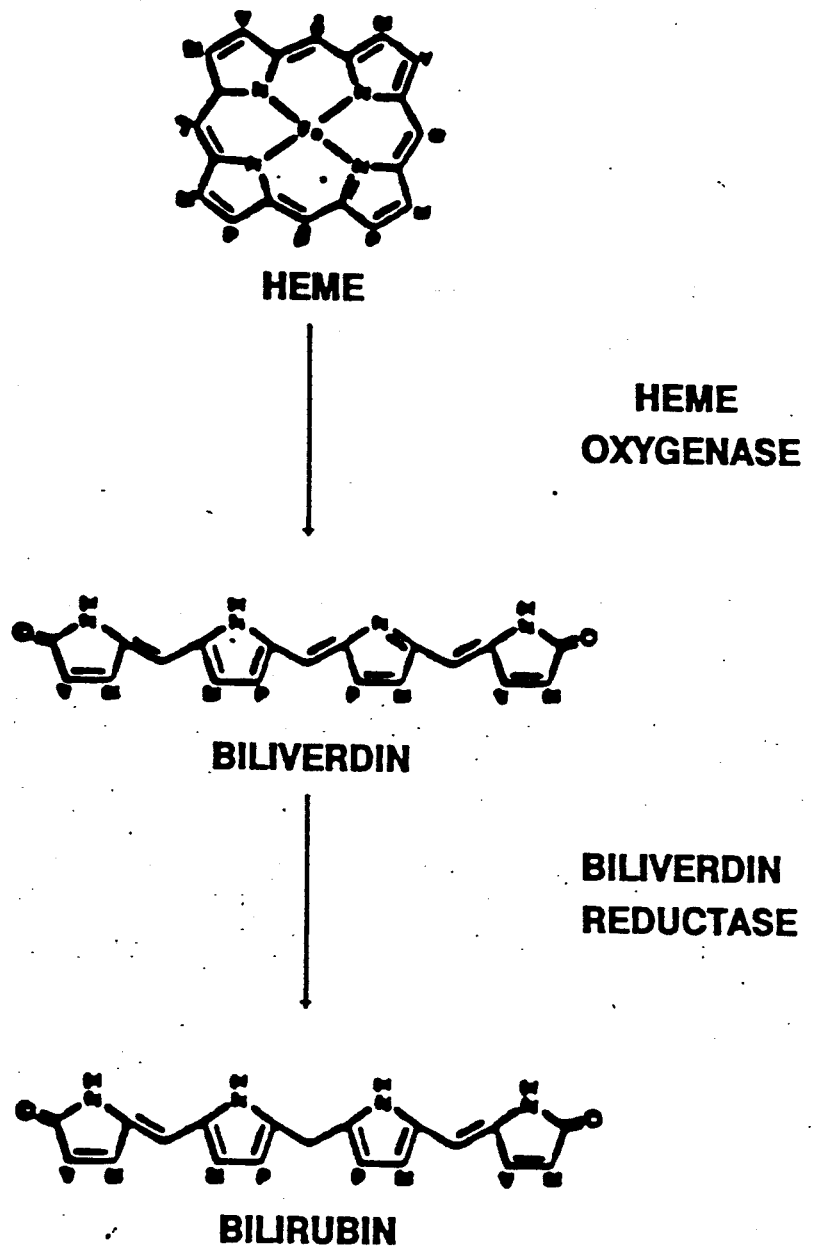
FIG. 5 schematically shows enzymatic inhibitor treatment according to one embodiment of the method of the present invention for processing whole blood for amplification.

In this example, the effect of enzymatic treatment of heme on inhibition of amplification is demonstrated. The reaction scheme is shown in FIG. 5. The enzymatic reaction is performed as follows. *Purification of Heme oxygenase.* Heme oxygenase is obtained from bovine spleen (T. Yoshinaga et al., J. Biol. Chem. 257:7778 (1982)), rat liver (R. K. Kutty and M. D. Maines J. Biol. Chem 257:9944 (1982)) or pig spleen or liver (T. Yoshida et al., J. Biochem 75:1187 (1974). The preferred source is pig and purification is as follows. Pig spleen or liver (about 1 kg) is homogenized in a Waring Blendor in 4 volumes of 0.134M KCl containing 0.02M potassium phosphate buffer (pH 7.4), and the homogenate is centrifuged successively for 15 min at 8,000×g, for 20 min at 18,000×g, and for 2 h at 56,000×g. The precipitates obtained are washed with 1.6 liters of 1 M KCl containing 20 mM potassium phosphate buffer (pH 7.4) and 10 mM EDTA by 2 h of centrifugation at 56,000×g. The resulting precipitates are suspended in 50 mM potassium phosphate buffer (pH 7.4) containing 10 mM EDTA to give a protein concentration of about 10 mg/ml. To this suspension is added sodium cholate (20% solution) at a ratio of 0.05 mg of sodium cholate to 1 mg of protein. After stirring for 20 min, the suspension is centrifuged for 90 min at 77,000×g. The precipitates are resuspended in 50 mM potassium phosphate buffer (pH 7.4) containing 1 mM EDTA to give a protein concentration of 10 mg/ml (the "microsome" fraction). The temperature is maintained at 0°–4° C. through this and other purification procedures. From 1 kg (wet weight) of pig spleen and pig liver, approximately 5 to 7 g and 8 to 10 g are obtained as microsomal protein, respectively. Further purification of heme oxygenase is usually started with 1,500 to 2,000 mg of pig spleen microsomes as protein which shows the specific activities of heme oxygenase in the range of 13.5 to 32.2 units/mg of protein. Heme oxygenase is solubilized from the microsomes by the addition of a 20% sodium cholate solution at a ratio of 1 mg of sodium cholate to 1 mg of protein. After stirring for 60 min, the suspension is centrifuged at 77,000×g for 90 min, and to the supernatant fluid (cholate fraction) is added solid ammonium sulfate up to 0.4 saturation. The precipitates collected by centrifugation are dissolved in 10 mM potassium phosphate buffer (pH 7.4), containing 1 mM EDTA, 0.1% Triton X-100, and 0.1% sodium cholate, so as to be twice the initial volume of the cholate fraction. Then the solution is applied to a column of DEAE-cellulose (DE23, 3×30 cm) previously washed with 10 mM potassium phosphate buffer (pH 7.4) containing mM EDTA, 0.1% Triton X-100, and 0.1% sodium cholate, and the column is washed with about 200 ml of 10 mM potassium phosphate buffer (pH 7.4) containing 70 mM KCl, 1 mM EDTA, 0.1% Triton X-100, and 0.1% sodium cholate. Heme oxygenase is eluted at a flow rate of 50 ml/h with 600 ml of a similar solution but increasing the KCl concentration linearly up to 310 mM, and 12-ml fractions are collected. The active heme oxygenase fractions (first DEAE-cellulose fraction) are combined and diluted 2.5-fold with cold distilled water and applied to a second DEAE-cellulose column (DE32, 2.6×28 cm) previously washed with 10 mM potassium phosphate buffer (pH 7.4) containing 1 mM EDTA, 0.1% Triton X-100, and 0.1% sodium cholate. After washing the column with 100 ml of the same buffer, heme oxygenase is eluted with 400 ml of a similar solution using a linear gradient between 0 and 200 mM in KCl, at a flow rate of 30 ml/h; 10-ml fractions are collected. The active fractions (second DEAE-cellulose fraction) are diluted 3-fold with cold distilled water and applied to a hydroxylapatite column (2.6×7 cm) previously washed with 10 mM potassium phosphate buffer (pH 7.4) containing 1 mM EDTA. The column is successively washed with 30 ml of 10 mM potassium phosphate buffer (pH 7.4) containing 1 mM EDTA, 50 ml of 200 mM potassium phosphate buffer (pH 7.4) containing 1 mM EDTA, 30 ml of 10 mM potassium phosphate buffer (pH 7.4) containing 1 mM EDTA, and 50 ml of 40 mM potassium phosphate buffer (pH 7.4) containing 1 mM EDTA, 0.1% Triton X-100, and 0.1% sodium cholate, at a flow rate of 50 ml/h. Elution of heme oxygenase from the column is performed with 100 ml of 100 mM potassium phosphate buffer (pH 7.4) containing 1 mM EDTA, 0.1% Triton X-100, and 0.1% sodium cholate at a flow rate of 30 ml/h; 7-ml fractions are collected. The active heme oxygenase fractions (hydroxylapatite fraction) are then applied to a column of Sephadex G-200 (5×90 cm) previously equilibrated with 30 mM potassium phosphate buffer (pH 7.4) containing 1 mM EDTA, 0.1% Triton X-100, and 0.1% sodium cholate. Heme oxygenase is eluted with the same equilibration buffer at a flow rate of 30 ml/h; 15-ml fractions are collected (Sephadex G-200 fraction).

When the Sephadex G-200 fraction is subjected to sodium dodecyl sulfate-polyacrylamide gel electrophoresis, only a single protein band showing an apparent molecular weight of 32,000 is observed. The purification reproducibly yields heme oxygenase preparations having a specific activity of about 5,200 to 5,650 units with an overall yield of 10 to 20%.

Purification of Biliverdin Reductase. The reductase is obtained from bovine spleen according to the protocol described by T. Yoshinaga et al., J. Biol. Chem. 257:7778 (1982). Fresh refrigerated bovine spleens (approximately 1 kg for each purification) are sliced and homogenized in a Waring blender with 4 volumes of 0.25M sucrose in 20 mM Tris-HCl, pH 7.4, containing 5 mM EDTA and 0.5 mM phenylmethylsulfonyl fluoride to inhibit proteolysis. Homogenates are centrifuged at 15,000×g for 20 min. Precipitates from the 15,000×g centrifugation are homogenized again with 2 volumes of the sucrose solution and centrifuged at 15,000 x g for 30 min. Supernatants thus obtained are centrifuged at 110,000×g for 60 minutes in a Beckman 60 Ti or a 50.2 Ti motor. Supernatant from the 110,000×g centrifugation of bovine spleen is fractionated from 35% to 65% saturation of ammonium sulfate, followed by column chromatography on DEAE-cellulose. The DEAE-cellulose fractions containing major enzyme activity are combined and concentrated and passed through a column of Sephacryl S-200. Further purification of biliverdin reductase is carried out by affinity chromatography on Sepharose coupled with 2',5'-ADP, a structural analogue of NADPH. The preparation obtained is colorless and typically will have a specific activity of at least 1100 units/mg of protein, showing a few minor protein bands when analyzed by SDS-polyacrylamide gel electrophoresis.

Inhibitor treatment. Enzymatic inhibitor treatment is performed with hemin. Heme oxygenase activity is determined by measuring the bilirubin formation on the basis of increase in absorbance at 468 nm. Standard reaction mixtures contain in a final volume of 2 ml: 200 μmol of potassium phosphate buffer (pH 7.4), 30 nmol of hemin, 0.2 mg of bovine serum albumin, excess amounts of a partially purified biliverdin reductase, 1 μmol of NADPH, appropriate amounts of NADPH-cytochrome c reductase partially purified from pig liver microsomes, and heme oxygenase preparation. The last two enzyme preparations contained 1 mM EDTA, 0.1% Triton X-100, and 0.1% sodium cholate, and the final concentrations of cholate and Triton X-100 in the incubation mixture were approximately 0.05%. NADPH is omitted in the control. The reaction is carried out for 5 to 10 min in a test tube placed in a shaking water bath at 37° C. The reaction is started by the addition of NADPH after a 2-min preincubation and stopped by immersing the tube in ice water. A value of 43.5 $mM^{-1}$ $cm^{-1}$ may be adopted as the extinction coefficient of bilirubin at 468 nm under these conditions. One unit of the enzyme is defined as the amount of enzyme catalyzing the formation of 1 nmol of bilirubin/h under the conditions described above.

EXAMPLE 6

As noted above, the present invention also contemplates an inhibitor treatment step that involves a combination of the above-named process steps. In this example, the inhibitor treatment comprises a process wherein both enzymatic and photochemical processes are employed in combination according to the present invention.

Figure 6:
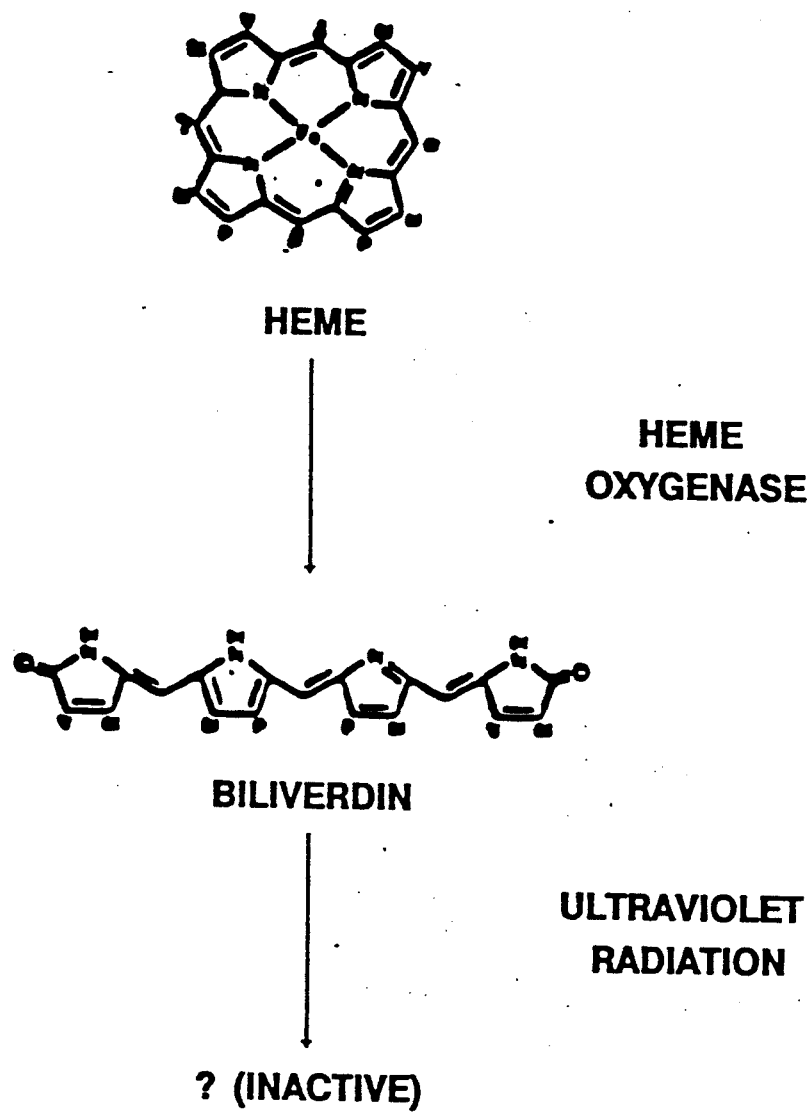
FIG. 6 schematically shows inhibitor treatment wherein both enzymatic and photochemical processes are employed in combination according to the present invention.

FIG. 6 schematically shows inhibitor treatment wherein both enzymatic and photochemical processes are employed in combination according to the present invention. In the first part of the scheme, heme-type inhibitors are treated with heme oxygenase and/or biliverdin reductase according to the protocol described in Example 4, above. Thereafter, the resulting product, biliverdin or bilirubin, is photochemically treated according to the protocol described in Example 2 and 3, above.

EXAMPLE 7

In this example, the inhibitor treatment comprises a process wherein both chemical and photochemical processes are employed in combination according to the present invention.

Figure 7:
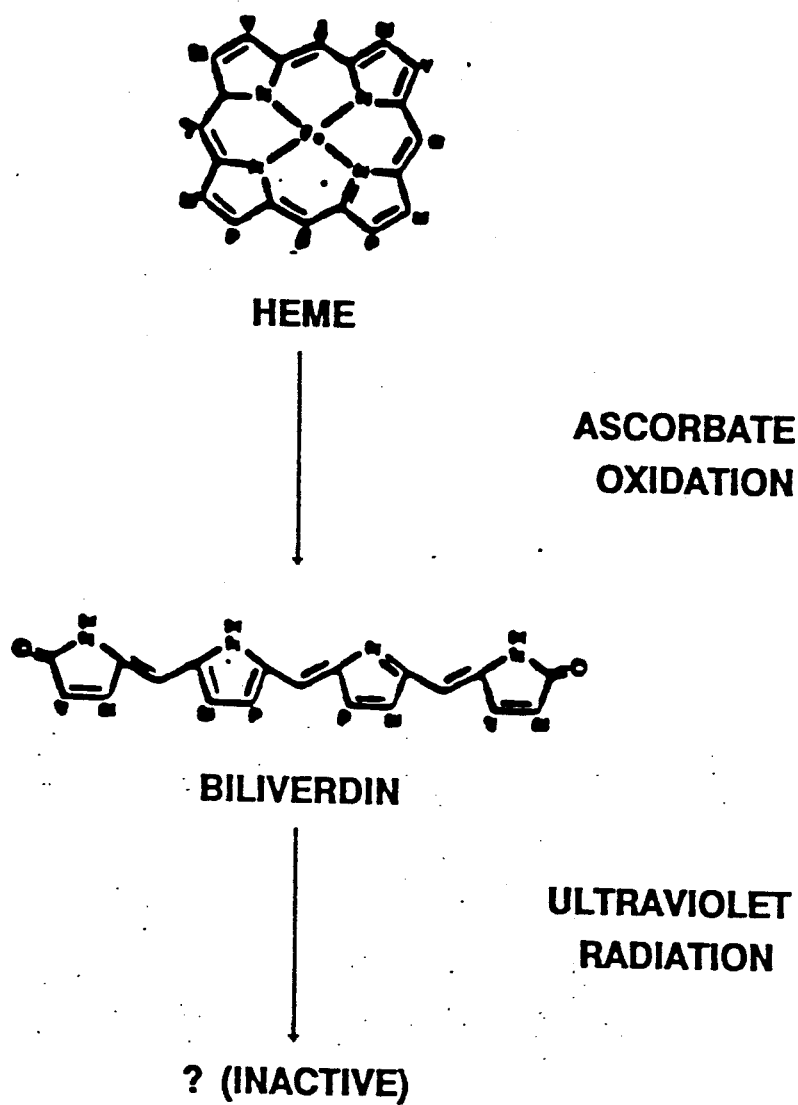
FIG. 7 schematically shows inhibitor treatment wherein both chemical and photochemical processes are employed in combination according to the present invention.

FIG. 7 schematically shows inhibitor treatment involving simultaneous use of chemical oxidation in the presence of ultraviolet radiation. The chemical oxidation involved the used of ascorbate. Heme undergoes coupled oxidation with ascorbate in the presence of a small quantity of apomyoglobin. Exposure of apomyoglobin to ascorbic acid and oxygen results in oxidative cleavage of the ring tetrapyrrole. The final product of heme is biliverdin. Biliverdin can thereafter be inactivated photochemically according to the protocol described in Example 2, above.

The reaction was performed as follows. Hemolyzed plasma was obtained by clearing hemolyzed blood by centrifugation at 12,000 rpm for 5 minutes in a microfuge. The total heme concentration was estimated to be 10 mM. Aliquots of "heme" solutions (0,500 μM) were made in 0.1M sodium phosphate buffer (pH 7.0) containing 8.4 mM ascorbate and with or without 82 μM apomyoglobin. Stock ascorbate (Sigma, 100 mg/ml) was solubilizd by adding 0.1N NaOH to pH 5.0. Tubes were incubated at 37° C. for 5 hours. Thereafter, half of the sample in each ascorbate tube was added to new tubes and these new tubes were treated photochemically using an HRI-100 for 4 hours using the industry standard, F8T5BL hot cathode dual bipin lamps.

Following irradiation of the new tubes, aliquots from all the tubes (corresponding to final heme concentrations of 125 μM, 25 μM, 5 μM, and 1μM) were added to standard (20 μl) PCR reactions in different tubes using the SK38/39 system (see above) and $10^9$ copies of 115-mer target. Standard control reactions were run in separate tubes. PCR was carried out for thirty (30) cycles. The PCR products were thereafter electrophoresed (agarose) and visualized with ethidium bromide staining. As expected, no product was visible with negative controls, while a product band corresponding to the expected 115-mer was apparent with the positive control (data not shown). The lanes corresponding to hemolyzed plasma tubes receiving no ascorbate showed no product, i.e. PCR was completely inhibited (data not shown). On the other hand, product was visible in all the lanes representing the reactions where ascorbate was added (except for the lanes corresponding to the very high concentration of heme, i.e. 125 μM). When the ascorbate tubes with no photochemical treatment were compared with those receiving irradiation, a stronger PCR product band was observed in those receiving irradiation.

Figure 8:
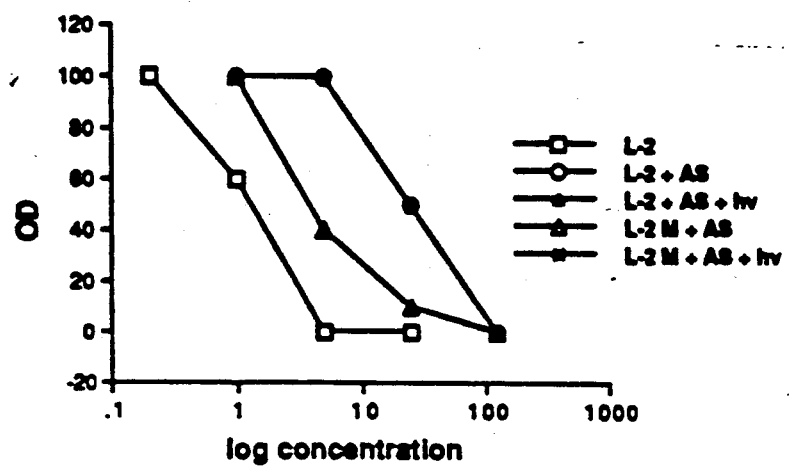
FIG. 8 is a graph showing quantitative changes in PCR signal following inhibitor treatment involving chemical and photochemical treatment in combination according to the present invention.

A quantitative analysis of the results is shown in FIG. 8. The graph is based on the best visual estimation of the band intensity. A score (i.e. % maximum intensity of a positve control) was given to each band. An OD of 1.0 corresponds to 100% of maximum intensity. After examination of a plot of the estimated OD units to the concentration of inhibitor (expressed in the log scale) in these PCR reactions, it is clear that approximately a thirty-fold reduction in inhibition was achieved with the combination of chemical oxidation and photochemical treatment.

EXAMPLE 8

In this example, the inhibitor treatment comprises an immunological process involving the preparation and use of monoclonal antibodies with reactivity for polymerase inhibitors. Mice may be injected with an antigenic amount, for example, from about 0.1 mg to about 20 mg of the inhibitor or antigenic parts thereof. Usually the injecting material is emulsified in Freund's complete adjuvant prior to injection. Boosting injections may also be required. A crude screen for antibody production can be carried out by testing the antisera on inhibitor. If antibody production is detected, a fusion is warranted. Lymphocytes can be obtained by removing the spleen of lymph nodes of sensitized animals in a sterile fashion and carrying out fusion.

A number of cell lines suitable for fusion have been developed and the choice of any particular line for hybridization protocols is directed by any one of a number of criteria such as speed, uniformity of growth characteristics, deficiency of its metabolism for a component of the growth medium, and potential for good fusion frequency. Intraspecies hybrids, particularly between like strains, work better than interspecies fusions. Several cell lines are available, including mutants selected for the loss of ability to secrete myeloma immunoglobulin.

Cell fusion can be induced either by virus, such as Epstein-Barr or Sendai virus, or polyethylene glycol. Polyethylene glycol (PEG) is the most efficacious agent for the fusion of mammalian somatic cells. PEG itself may be toxic for cells and various concentrations should be tested for effects on viability before attempting fusion. The molecular weight range of PEG may be varied from 1000 to 6000. It gives best results when diluted to from about 20% to about 70% (w/w) in saline or serum-free medium. Exposure to PEG at 37° C. for about 30 seconds is preferred in the present case, utilizing murine cells. Extremes of temperature (i.e., about 45° C.) are avoided, and preincubation of each component of the fusion system at 37° C. prior to fusion can be useful. The ratio between lymphocytes and malignant cells is optimized to avoid cell fusion among spleen cells and a range of from about 1:1 to about 1:10 is commonly used.

The successfully fused cells can be separated from the myeloma line by any technique known by the art. The most common and preferred method is to choose a malignant line which is Hypoxthanine Guanine Phosphoribosyl Transferase (HGPRT) deficient, which will not grow in an aminopterin-containing medium used to allow only growth of hybrids and which is generally composed of hypoxthanine $1 \times 10^{-4}$M, aminopterin $1 \times 10^{-5}$M, and thymidine $3 \times 10^{-5}$M, commonly known as the HAT medium. The fusion mixture can be grown in the HAT-containing culture medium immediately after the fusion 24 hours later. The feeding schedules usually entail maintenance in HAT medium for two weeks and then feeding with either regular culture medium or hypoxthanine, thymidine-containing medium.

The growing colonies are then tested for the presence of antibodies that recognize inhibitors. Detection of hybridoma antibodies can be performed using an assay where the inhibitor is bound to a solid support and allowed to react to hybridoma supernatants containing putative antibodies. The presence of antibodies may be detected by "sandwich" techniques using a variety of indicators. Most of the common methods are sufficiently sensitive for use in the range of antibody concentrations secreted during hybrid growth.

Cloning of hybrids can be carried out after 21-23 days of cell growth in selected medium. Cloning can be preformed by cell limiting dilution in fluid phase or by directly selecting single cells growing in semi-solid agarose. For limiting dilution, cell suspensions are diluted serially to yield a statistical probability of having only one cell per well. For the agarose technique, hybrids are seeded in a semi-solid upper layer, over a lower layer containing feeder cells. The colonies from the upper layer may be picked up and eventually transferred to wells.

Antibody-secreting hybrids can be grown in various tissue culture flasks, yielding supernatants with variable concentrations of antibodies. In order to obtain higher concentrations, hybrids may be transferred into animals to obtain inflammatory ascites. Antibody-containing ascites can be harvested 8-12 days after intraperitoneal injection. The ascites contain a higher concentration of antibodies but include both monoclonals and immunoglobulins from the inflammatory ascites. Antibody purification may then be achieved by, for example, affinity chromatography.

The utilization of an antibody produced in the above-described manner is accomplished by providing antibody on a solid support and passing the products of the non-selective lysis step over the solid support. Where antibody is coupled to a solid support, it may be covalently or passively bound. The solid support is typically glass or a polymer, the most commonly used polymers being cellulose, polyacrylamide, nylon, polystyrene, polyvinyl chloride or polypropylene. The solid support may be in the form of tubes, beads, discs or microplates. Antibody coupling processes are well-known in the art as described by Quash, U.S. Pat. Nos. 4,419,444 and 4,217,338, and Forrest et al., U.S. Pat. No. 4,659,678, hereby incorporated by reference.

To perform the non-selective lysis protease K is used (e.g. Sigma, St. Louis, Mo., U.S.A., catalogue No. p4914 "Proteinase K"). In this reaction, 5 µl of whole blood is added to 20 µl of PK mix (10 mM Tris pH 8.0, 1.0 mM EDTA, 0.5% Tween 20, 0.5% NP40, and PK). A high concentration of protease K (2.5 mg/ml) is used for 5 minutes at 55° C. to completely degrade cellular as well as plasma protein and expose cellular nucleic acid for amplification. So that amplification may be carried out, protease K is inactivated by heating the mixture at 95° C. for 5 minutes.

The reaction can thereafter be added to a small column containing the antibody on the solid support. The inhibitors will bind to the antibody. Repeated passes of the reaction mixture will eliminate the inhibitors.

EXAMPLE 9

Figure 9:
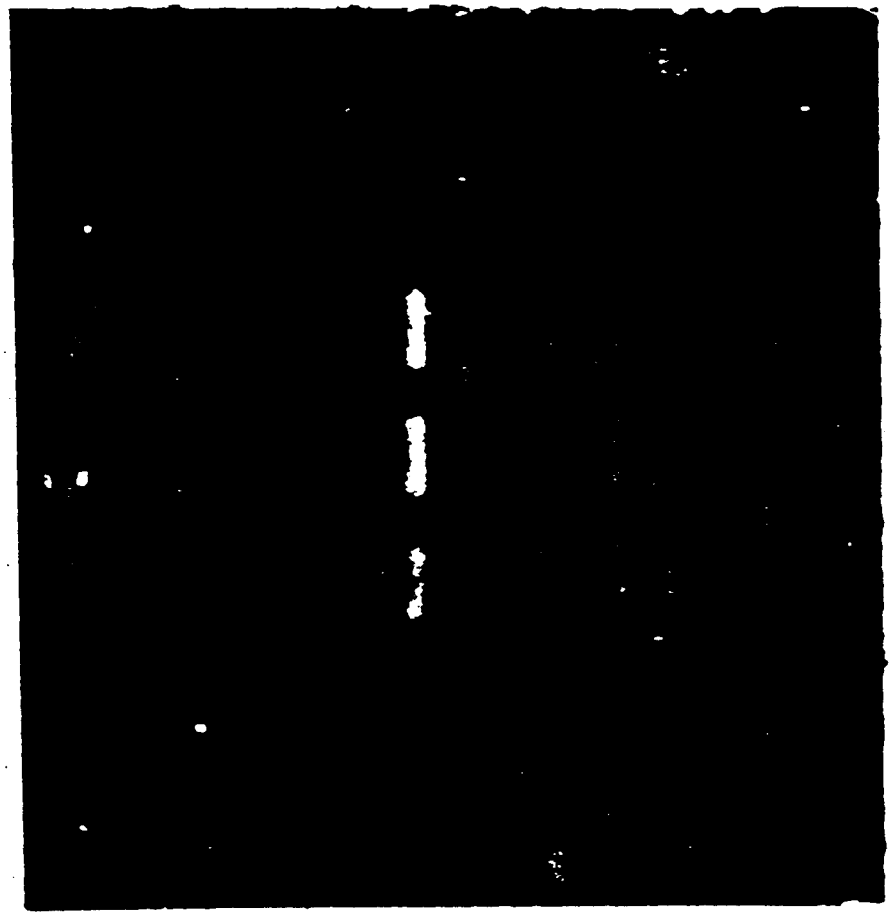
FIG. 9 is a (direct print) photograph of an ethidium bromide stained gel of electrophoresed PCR-amplified HIV sequences showing the impact of the presence of reagents used for the selective lysis step (see FIG. 1) of the present invention with respect to amplification inhibition.

In this example, the presence of the diluent and lysis agent used for the selective lysis step (see FIG. 1) is examined with respect to amplification inhibition. Aliquots of different amounts of ISOTON®II, a diluent manufactured by Coulter Diagnostics, and the commercial selective cell lysis agent ZAP-OGLOBIN® (also manufactured by Coulter Diagnostics) were added to standard (20 µl) PCR reactions in different tubes using the SK38/39 system (see above). Three standard control reactions were run in separate tubes: i) a no nucleic acid target control, ii) a no primer control, and iii) a positive control (no diluent or lysis agent). PCR was carried out for 30 cycles. The PCR products were thereafter electrophoresed (agarose) and visualized with ethidium bromide staining (FIG. 9, lanes 1-7). The three above-named control reactions were electrophoresed in lanes 1, 2 and 3, respectively. As expected, no product is visible in lanes 1 and 2 (negative controls), while a strong product band corresponding to the expected 115-mer is apparent in lane 3 (positive control). The lanes (lanes 3 and 4) corresponding to tubes where ISOTON®II was added at 25% and 10%, repsectively, also show a strong product band corresponding to the expected 115-mer. By contrast, the lane (lane 6) corresponding to tubes where ZAP-OGLOBIN® was at 5% show no product, and the lane (lane 7) corresponding to tubes where ZAP-OGLOBIN® was at 0.5% shows a very faint product band. It is apparent that the lysing agent contains polymerase inhibitors and that, after selective lysis, it is desired that less than 0.5% should be present in the tube when amplification is initiated.

EXAMPLE 10

In this example, the steps of Mode Ib (see FIG. 1) of the method of the present invention are performed to obtain nucleic acid from whole blood. Different amounts ($4\times 10^3$, $2\times 10^3$, $2\times 10^2$, $2\times 10^1$, 2, 0.2, and 0) of HIV-infected H9 cells were added to 0.1 ml of whole blood. For each amount of H9 cells, the steps are carried out in the same reaction vessel (e.g. Eppendorf tube). The blood was diluted (1:10) with ISOTON®II (Coulter Diagnostics) and the red cells were selectively lysed by the addition of 4 µl of ZAP-OGLOBIN® (Coulter Diagnostics). The white cells were concentrated by centrifuging the lysate to create a white cell pellet and a supernatant. The supernatant was removed and the pellet was resuspended in ISOTON®II (i.e. the cells were washed). Following a second centrifugation and wash, the cells were pelleted and thereafter lysed by the addition of protease K (55° C. for 1 hour). The protease was inactivated by heating at 95° C for 10 minutes.

Aliquots of the lysate were added to standard (20 µl) PCR reactions in different tubes using the SK38/39 system (see above). Two standard control reactions were run in separate tubes: i) a no nucleic acid target control, and ii) a positive control ($10^9$ copies of 115-mer in a 100 µl PCR reaction). PCR was carried out for 30 and 40 cycles. The PCR products were thereafter electrophoresed (agarose) and visualized with ethidium bromide staining (FIG. 10A, 30 cycles; FIG. 10B, 40 cycles). The two above-named control reactions were electrophoresed in lanes 8 and 9, respectively. As expected, no product is visible in lane 8 (negative control), whether 30 cycles or 40 cycles were used. A strong product band corresponding to the expected 115-mer is apparent in lane 9 (positive control). The lanes corresponding to tubes where HIV-infected H9 cells were added in decreasing amounts (lanes 1-7) show a corresponding decrease in product band signal. Signal falls of at approximately 2 cells (see lane 5, FIG. 10B) (the signals in lane 6 and 7 of 40 cycles, FIG. 10B, may be due to carryover). It is clear that viral sequences can be recovered and thereafter amplified from whole blood according to Mode Ib of the method of the present invention.

EXAMPLE 11

In this example, the steps of Mode Ia and Mode Ib (see FIG. 1) of the method of the present invention are performed to obtain nucleic acid from whole blood using a filter. Different amounts (0, 1, 5 and 10µl) of stored (21 day old) whole blood were diluted in 1 ml of ISOTON®II (Coulter Diagnostics) and the red cells were selectively lysed by the addition of 4 µl of ZAP-OGLOBIN® (Coulter Diagnostics). The lysate was thereafter filtered through a LOPRODYNE® filter (Pall, Glen Cove, N.Y.) nylon membrane filter in a multi-welled filtration manifold ("The Minifold I", Schleicher & Schuell, Keene, N.H., U.S.A.) (the 10µl samples would not filter completely). The immobilized white cells on the filter were thereafter washed (3×) with 250 µl ISOTON®II. The filters were then removed and transferred to 0.5 ml Eppendorf tubes. The immobilized cells were lysed by the addition of protease K (2.5 mg/ml, 55° C. for 10 minutes) to create a second lysate. The protease was inactivated by heating at 95° C. for 10 minutes.

Aliquots of the protease K lysate were added to 100 µl PCR reactions in different tubes using the using primer pair GH26/GH27 to produce a 242-mer product (see above). Two sets of PCR reactions were set up: 1) no inhibitor treatment (Mode Ib, FIG. 1); and 2) inhibitor treatment (Mode Ia, FIG. 1). Inhibitor treatment involved the addition of bovine transferrin and the cofactor sodium bicarbonate prior to amplification. Two standard control reactions were run in separate tubes: i) a positive control (human placental DNA) and ii) a no nucleic acid target control. PCR was carried out for 35 cycles. The PCR products were thereafter electrophoresed (agarose) and visualized with ethidium bromide staining (FIG. 11A, inhibitor treatment; FIG. 11B, no inhibitor treatment). The two above-named control reactions were electrophoresed in lanes marked "P" and "N", respectively. As expected, no product is visible with the negative control. A strong product band corresponding to the expected 242-mer is apparent in the positive control. The lanes corresponding to (duplicate) tubes where different amounts (1, 5 and 10μl) of whole blood cells were added in (lanes 3-4, 5-6 and 7-8, respectively) show a corresponding increase in product band signal, with and without inhibitor treatment (compare 11A with 11B). Lanes 1-2 correspond to the no blood samples. As expected, no product is visible. Thus, it is clear that with adequate washing on a filter, Mode Ib is an alternative to Mode Ia.

EXAMPLE 12

In this example, the steps of Mode Ia (see FIG. 1) of the method of the present invention are performed to obtain nucleic acid from whole blood in a low copy system (HIV). Whole blood (100 μl) was diluted in 1 ml of ISOTON®II (Coulter Diagnostics) and the red cells were selectively lysed by the addition of 4 μl of ZAP-OGLOBIN® (Coulter Diagnostics). The white cells were concentrated by centrifuging the lysate to create a white cell pellet and a supernatant. The supernatant was removed and the pellet was resuspended in ISOTON-®II (i.e. the cells were washed). Following a second centrifugation and wash, the cells were pelleted and thereafter lysed by the addition of protease K (5 mg/ml, 55° C. for 1 hour). The protease was inactivated by heating at 95°-100° C. for 10 minutes.

Figure 12:
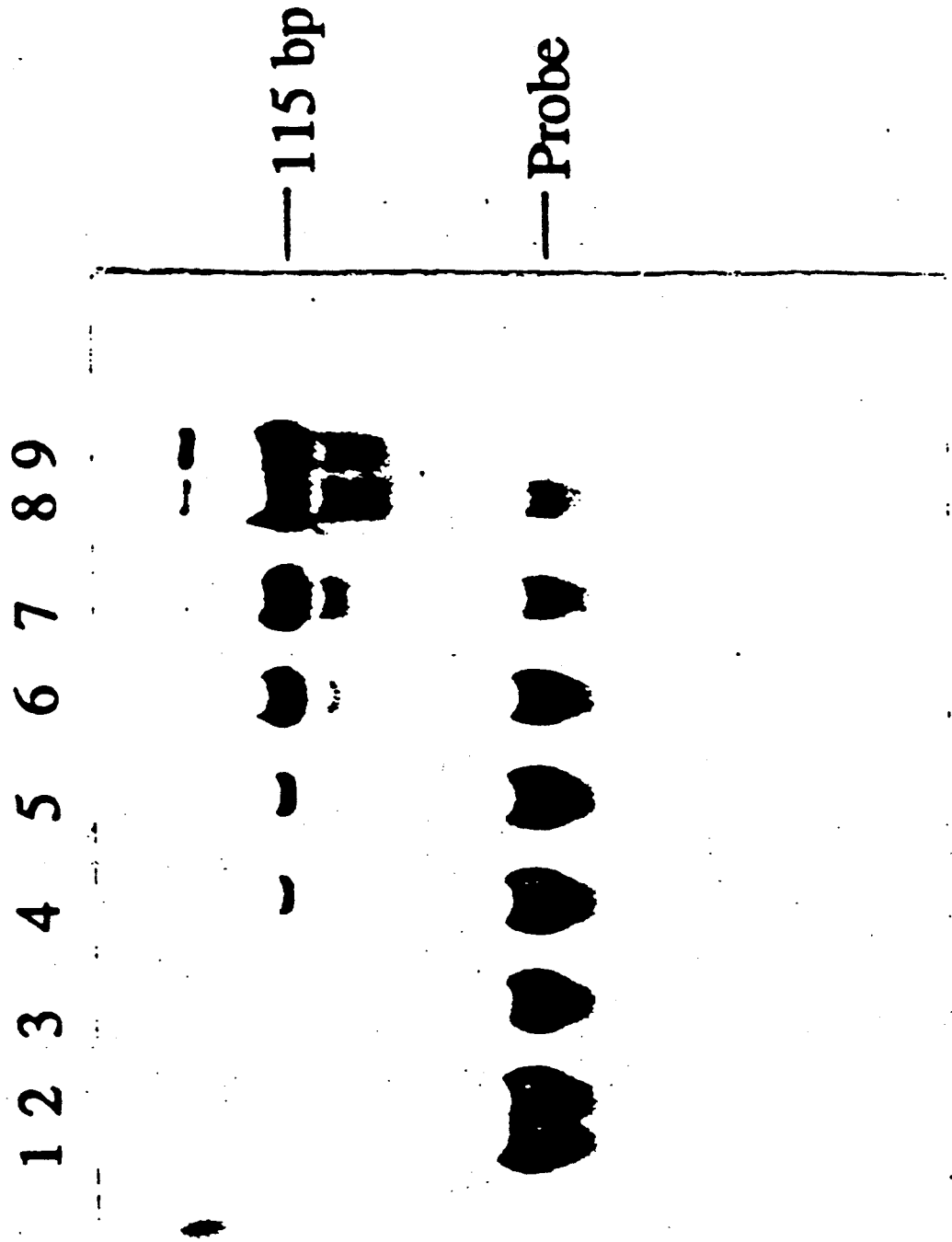
FIG. 12 is a photograph of an autoradiograph of electrophoresed, PCR-amplified, HIV sequences visualized by oligonucleotide hybridization analysis following the steps of Mode Ia (see FIG. 1) of the method of the present invention

Different amounts ($2 \times 10^3$, $10^3$, $10^2$, $10^1$, 5, 1 and 0) of HIV-infected H9 cells were then added to the protease K lysate. For each amount of H9 cells, the steps are carried out in the same reaction vessel (e.g. Eppendorf tube). Thereafter bovine transferrin and the cofactor sodium bicarbonate were added to each tube, along with PCR reagents to a final volume of 100 μl. PCR reactions were carried out using the SK38/39 system (see above). Two standard control reactions were run in separate tubes: i) a no nucleic acid target control, and ii) a positive control ($10^9$ copies of 115-mer in a 100 μl PCR reaction). PCR was carried out for 35 cycles. The products were electrophoresed and viualized by oligonucleotide hybridization analysis and autoradiography (FIG. 12). The two above-named control reactions were electrophoresed in lanes 1 and 9, respectively. As expected, no product (only radiolabelled probe) is visible in lane 1 (negative control). A strong product band corresponding to the expected 115-mer is apparent in lane 9 (positive control). The lanes corresponding to tubes where HIV-infected H9 cells were added in increasing amounts (lanes 2-8) show a corresponding increase in product band signal. Signal falls of at approximately 5 cells (see lane 3, FIG. 12) (there is signal in lanes 2, corresponding to 1 cell, corresponding to 1 and 0 cells, respectively). It is clear that viral sequences can be recovered and thereafter amplified from whole blood according to Mode Ia of the method of the present invention.

EXAMPLE 13

In this example, the steps of Mode III (see FIG. 1) of the method of the present invention are performed to obtain nucleic acid from whole blood. Whole blood samples were lysed with protease K (500 μg/ml, 55° C. for 1 hour). The enzyme was inactivated by heating (95°-100° C., 10 minutes). Aliquots corresponding to 25,000, 10,000, 5,000, 2,000, 1000, 500 and 0 cells were made. Bovine transferrin (250 μg) was added to each sample as well as the cofactor sodium bicarbonate (adjusted to 10 mM) and the reaction was incubated at room temperature for 30 minutes. Concentrated PCR reagents were then added to each sample to a final volume of 100 μl. Three standard control reactions were run in separate tubes: i) a no nucleic acid target control, ii) a no primer control, and iii) a positive control (0.2 μg of human placental DNA). In addition, three additional tubes (corresponding to 25,000, 5,000 and 0 cells) were left untreated (no transferrin or cofactor). PCR was performed for 35 cycles using globin primer set KM-29/HRI-12. The PCR products were thereafter electrophoresed (agarose) and visualized with ethidium bromide staining (FIG. 13, lanes 1-13). The three above-named control reactions were electrophoresed in lanes 11, 12 and 13, respectively. As expected, no product is visible in lanes 11 and 12 (negative controls), while a strong product band corresponding to the expected 174-mer is apparent in lane 13 (positive control). The lanes (lanes 4-10) corresponding to tubes where inhibitor treatment was performed show a decreasing product band corresponding to the decreasing amount of cells. By contrast, the lanes (lanes 1-3) corresponding to tubes where no inhibitor treatment was performed show no product. It is apparent that the inhibitor treatment is critical for amplification.

EXAMPLE 14

In this example, the steps of Mode Ib and Mode III (see FIG. 1) of the method of the present invention are compared for sensitivity and specificity.

Mode Ib. Different amounts ($10^4$, $10^3$, $10^2$, $10^1$, and 0) of HIV-infected H9 cells were added to 1 ml of diluted whole blood. For each amount of H9 cells, the steps are carried out in the same reaction vessel (e.g. Eppendorf tube). The blood was diluted (1:10) with ISOTON®II (Coulter Diagnostics) and the red cells were selectively lysed by the addition of 4 μl of ZAP-OGLOBIN® (Coulter Diagnostics). The white cells were concentrated by centrifuging the lysate to create a white cell pellet and a supernatant. The supernatant was removed and the pellet was resuspended in ISOTON®II (i.e. the cells were washed). Following a second centrifugation and wash, the cells were pelleted and thereafter lysed by the addition of protease K (55° C. for 1 hour). The protease was inactivated by heating at 95° C for 10 minutes.

Mode III. Different amounts ($2 \times 10^4$, $2 \times 10^3$, $10^3$, $5 \times 10^2$, $2 \times 10^2$, $10^2$, $5 \times 10$, 10 and 0) of HIV-infected H9 cells were added to 50 μl of whole blood. For each amount of H9 cells, the steps are carried out in the same reaction vessel (e.g. Eppendorf tube). Whole blood samples were lysed with protease K (500 μg/ml, 55° C. for 1 hour). The enzyme was inactivated by heating (95°-100° C., 10 minutes). Bovine transferrin was added to each sample as well as the cofactor sodium bicarbonate and the reaction was incubated at room temperature for 30 minutes.

No Blood Controls. Different amounts ($10^4$, $10^3$, $10^2$, $10^1$, and 0) of HIV-infected H9 cells were added to uninfected H9 cells in 1 ml of ISOTON®II and were further processed for comparison.

Figure 14B:
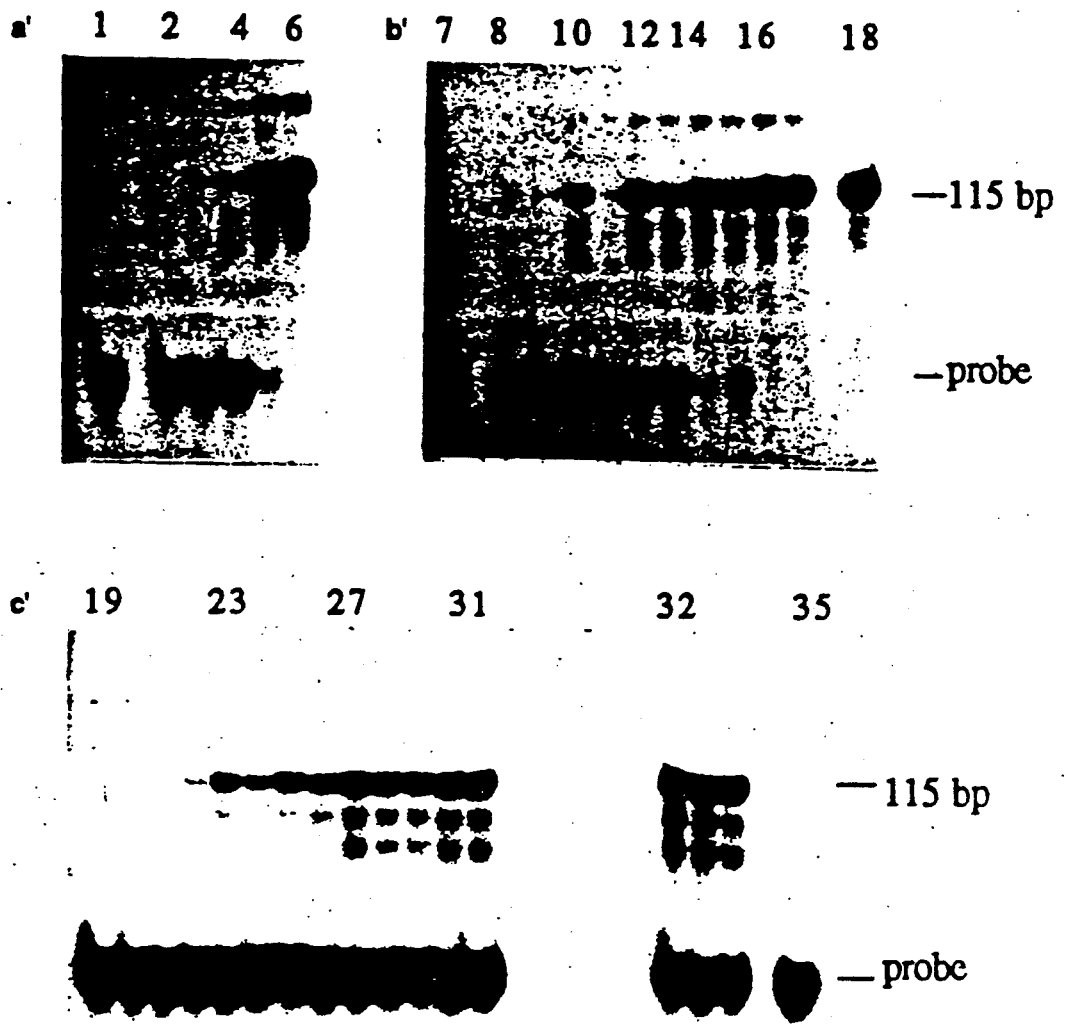
FIGS. 14B(A'-C') are photographs of an autoradiograph of electrophoresed, PCR-amplified, HIV sequences visualized by oligonucleotide hybridization analysis comparing the specificity and sensitivity of amplifications following the steps of Mode Ib and Mode III (see FIG. 1) of the method of the present invention.

Amplifications. Both HLA and HIV PCRs were run as described in earlier examples. Standard control reactions were run in separate tubes. The PCR products were thereafter electrophoresed (agarose) and visualized with ethidium bromide staining (FIG. 14A) or they were electrophoresed (PAGE) and visualized with OH and autoradiograph (FIG. 14B). Suprisingly, the addition of transferrin improves the specificity of the reaction (see FIG. 14A, compare lanes 3-17 of a' with 1-16 of b'), i.e. the lanes corresponding to tubes where inhibitor treatment was performed (Mode III) show a clean product band while the lanes corresponding to tubes where no inhibitor treatment was performed (Mode 1b) show nonspecific amplification of a number products. It is apparent that the inhibitor treatment has some impact on amplification specificity.

Sensitivity is examined in FIG. 14B. The no blood controls are in lanes 1-6 (see FIG. 14B, a'). A signal is seen corresponding to 1 HIV-infected cell. Mode 1B results are shown in FIG. 14B (b') and Mode III results are shown in FIG. 14B (c'); both show that a signal can be detected with as little as one HIV-infected cell.

The ability of transferrin to overcome inhibition extends even to amplification involving thermal cycling. It is not clear how transferrin is able to continue functioning after exposure to such high temperatures.

EXAMPLE 15

In this example, different sources of transferrin are examined. FIG. 15 is a (direct print) photograph of an ethidium bromide stained gel of electrophoresed PCR-amplified, HIV sequences following inhibitor treatment with rat (lanes 2-4), rabbit (lanes 5-7) and bovine (lanes 8-10) transferrin in the presence of the cofactor sodium bicarbonate. It is clear that rat transferrin does not work as an interfering reagent.

EXAMPLE 6

Figure 16A:
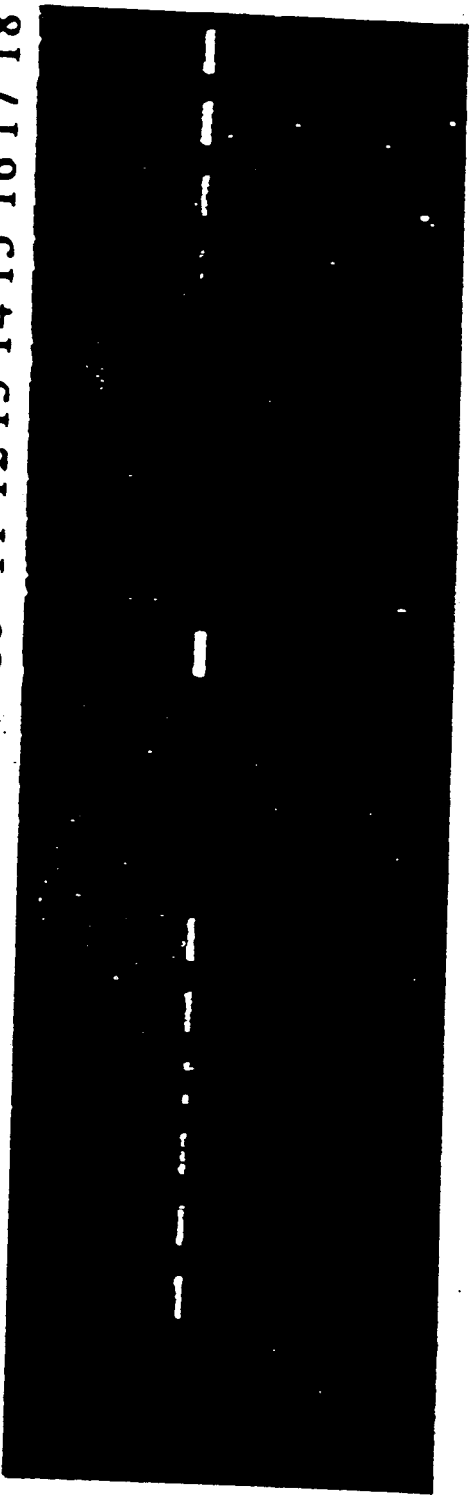
FIGS. 16A, B & C are (direct print) photographs of an ethidium bromide stained gel of electrophoresed PCR-amplified, HLA class II gene sequences following biochemical inhibitor treatment according to embodiments of, the method of the present invention.

In this example, transferrin and serum albumin are compared in the method of the present invention. Whole blood was prepared according to Mode III (see FIG. 1). Whole blood samples (100 µl) were lysed with protease K (0.55 mg/ml, 55° C. for 1 hour). The enzyme was inactivated by heating (95°-100° C., 10 minutes). Four sets of reactions were then set up involving the addition of interfering reagent to the protease lysate: 1) transferrin with 10 mM sodium bicarbonate; 2) transferrin with 20 mM sodium bicarbonate; 3) serum albumin with 10 mM sodium bicarbonate; 4) serum albumin with no cofactor. These reaction were performed at room temperature for thirty minutes using a concentration range for transferrin and serum albumin (10, 25, 50, 75, 100, 150, 200 and 250 µg per 20 m PCR reaction). PCR was then set up using the primer pair GH26/GH27 to produce a 242-mer product (see above). Two standard control reactions were run in separate tubes: i) a no nucleic acid target control; and 2) a positive control (human placental DNA). Six additional control lanes were run: 1) no inhibitor treatment (two lanes); 2) 10 mM sodium bicarbonate only (one lane); 3) 50 µg transferrin with 10 mM sodium bicarbonate (two lanes). PCR was carried out for 35 cycles. The PCR products were thereafter electrophoresed (agarose) and visualized with ethidium bromide staining. The two above-named control reactions were electrophoresed in lanes 9 and 10 of FIG. 16A, respectively, as well as lanes 17 and 18 of FIG. 16B, respectively. In FIG. 16C, the positive control is in lane 1 and the negative control is in lane 2. As expected, no product is visible with the negative control. A strong product band corresponding to the expected 242-mer is apparent in the positive control.

FIG. 16A shows the impact of transferrin as a function of concentration. Lanes 1-8 of FIG. 16A correspond to 10, 25, 50, 75, 100, 150, 200 and 250 µg of transferrin in the presence of cofactor. No product is visible with 10 µg transferrin (lane 1), while a faint product band is visible with 25 µg (lane 2). Strong product bands are visible at the higher concentrations (lanes 3-8). Interestingly, however, product bands are not as apparent with the higher concentration of the cofactor (lanes 11-18).

Figure 16B:
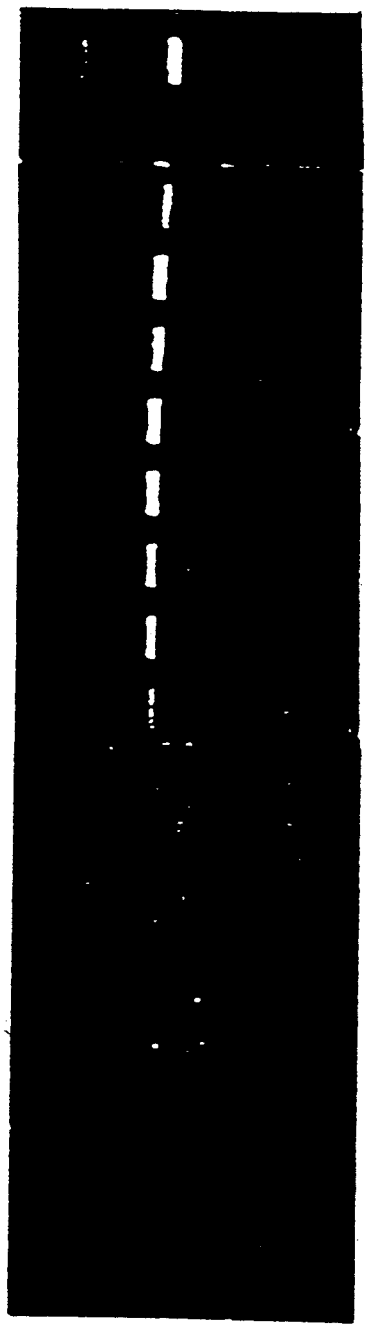

FIG. 16B shows the impact of serum albumin as a function of concentration. Lanes 1-8 of FIG. 16B correspond to 10, 25, 50, 75, 100, 150, 200 and 250 µg of serum albumin without cofactor. No product is visible in any of these lanes. Serum albumin with cofactor, however, does show product (lanes 9-16). While a weak product band is visible with 25 µg (lane 9), strong product bands are visible at the higher concentrations (lanes 10-16).

FIG. 16C shows the results of the additional control lanes. Lanes 3-4 of FIG. 16C correspond to no inhibitor treatment and no product bands are evident. No product is visible with 10 mM of cofactor alone (lane 5) or with 50 µg of transferrin alone (lane 6). Strong product bands are visible with 50 µg of transferrin with 10 mM cofactor (lanes 7-8).

From the above it should be clear that a cofactor is critical for both transferrin and serum albumin to overcome polymerase inhibitors. Interestingly, the cofactor concentration must be selected for optimal effect.

EXAMPLE 17

Figure 17:
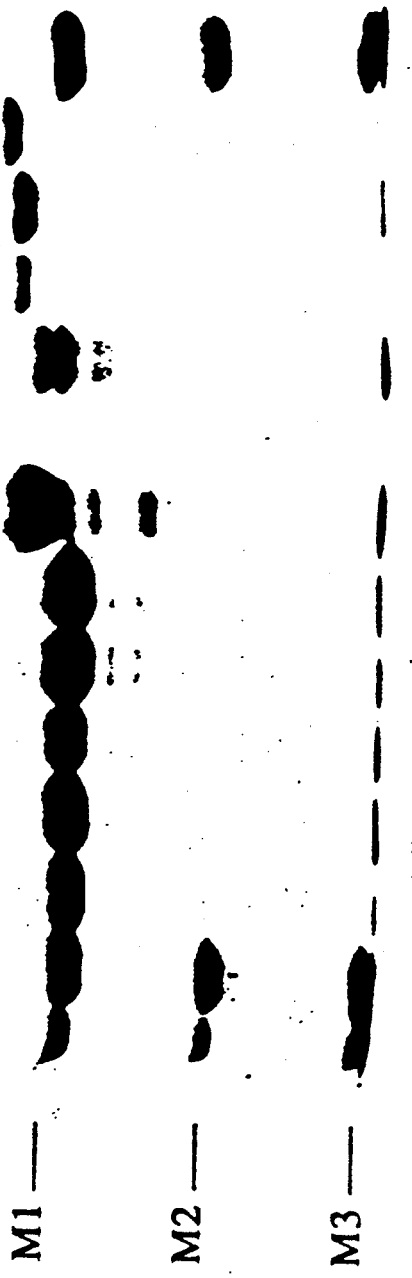
FIG. 17 is a photograph of a Coomassie blue stained, SDS-PAGE gel of fractionated compounds of the present invention.
Figure 18:
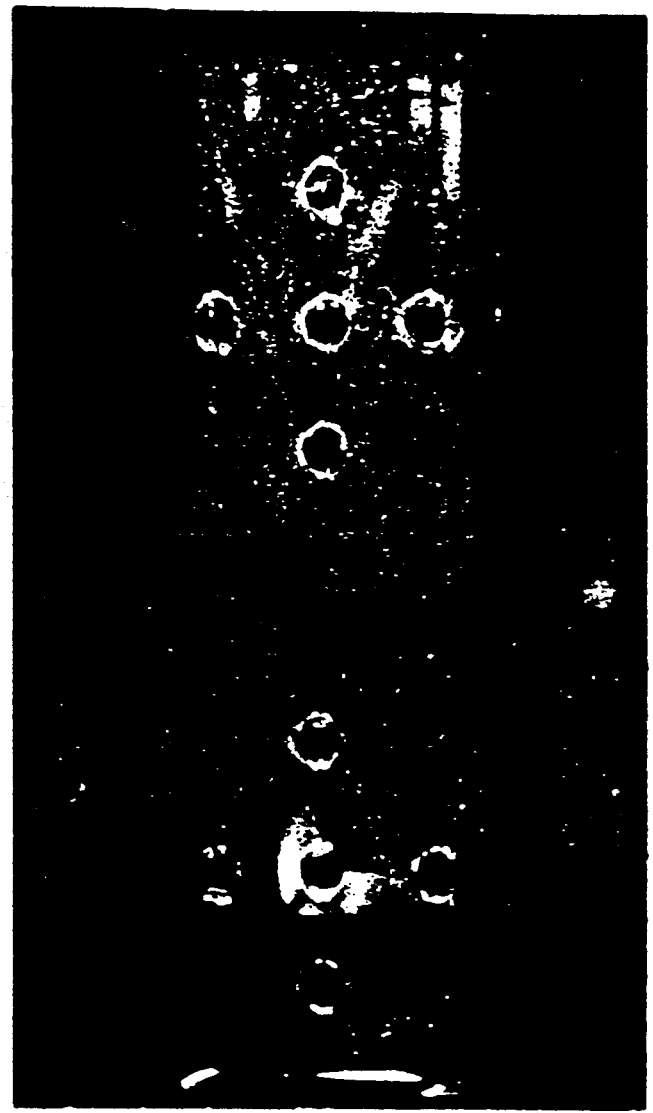
FIG. 18 is a photograph of an Ouchterlony immunodiffusion gel showing the formation of precipitin lines where antibody has reacted with some of the compounds of the present invention.

In this example, transferrins and serum albumins are examined by SDS-PAGE (see above for SDS-PAGE protocol). After electrophoresis, the protein bands were visualized with Coomassie blue (Sigma) in 50% Methanol and 10% trichloroacetic acid for 1 hour followed by destaining in 5% methanol and 7% acetic acid (FIG. 17). Lanes 1, 2, and 14 are molecular weight markers. M1 is bovine albumin. M2 is egg albumin. M3 is trypsinogen. Lanes 3-7 are commercial serum albumin preparations. Lanes 8-13 correspond to transferrins from different sources (human, horse, bovine, mouse, rat, and rabbit, respectively).

It is clear that all of the bovine serum albumin preparations are nearly uniform. On the other hand, the transferrins are different from the serum albumins (i.e. higher molecular weight) as well as from one another.

EXAMPLE 18

In this example, transferrins and serum albumins are examined immunologically (see Ouchterlony protocol). A solution of antibody reactive with bovine serum albumin (Sigma, St. Louis, Mo., U.S.A.) was placed in the center well ("0") and solutions of the relevant test samples were placed separately in the surrounding wells. Wells 1 and 2 contained commercial preparations of bovine serum albumin.

Wells 3-8 contained commercial preparations of transferrins from different sources (human, horse, bovine, mouse, rat, and rabbit, respectively). The inspection of the petri dish revealed the presence of precipitin lines only with the serum albumin wells). This indicates that the antibody only reacted with serum albumin and not transferrin. It is clear that all of the transferrins are different from the serum albumins.

EXAMPLE 19

Figure 19:
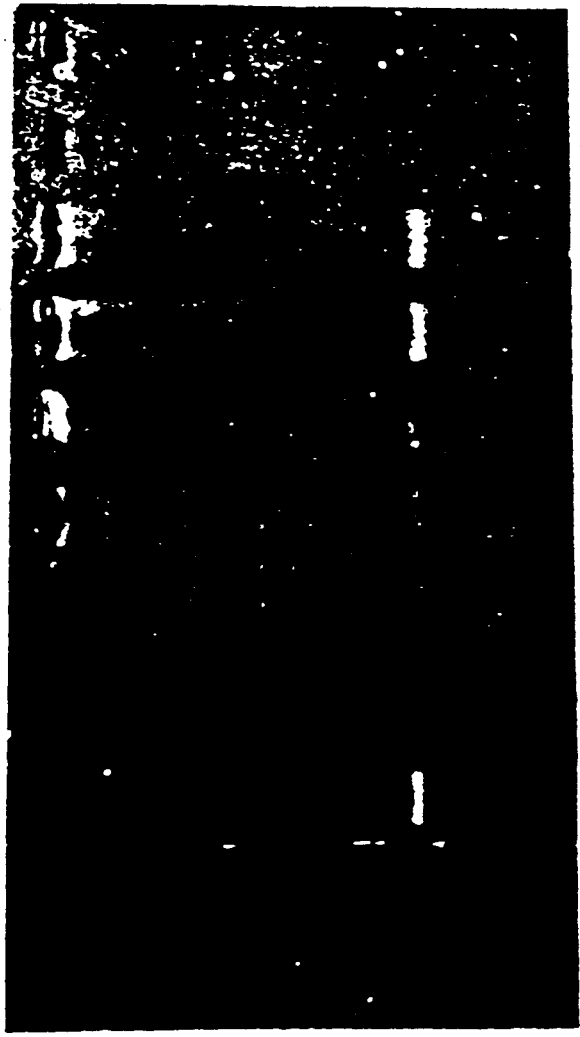
FIG. 19 is a (direct print) photograph of an ethidium bromide stained gel of electrophoresed PCR-amplified, HIV sequences following biochemical inhibitor treatment according to one embodiment of the method of the present invention.

In this example, the effect of biochemical treatment of hematin is compared with biochemical treatment of the non-metal-containing porphyrin "protoporphyrin." Stock solutions of 500 μM hematin (Sigma) or 500 μM protoporphyrin (Sigma) were used to set up four reactions in duplicate: 1) hematin only, 2) protoporphyrin only, 3) protoporphyrin with 50 μg bovine transferrin with cofactor, and 4) protoporphyrin with 100 μg bovine transferrin with cofactor. Following the reaction (30 mintes at room temperature) PCR reagents were added to the tubes and standard (20 μl) PCR reactions were carried out using the SK38/39 system (see above). Three standard control reactions were run in separate tubes: i) a no nucleic acid target control, ii) a no primer control, and iii) a positive control (no hematin). PCR was carried out for 30 cycles. The PCR products were thereafter electrophoresed (agarose) and visualized with ethidium bromide staining (FIG. 19). The three above-named control reactions were electrophoresed in lanes 1, 2 and 3, respectively. As expected, no product is visible in lanes 1 and 2 (negative controls), while a strong product band corresponding to the expected 115-mer is apparent in lane 3 (positive control). The "hematin only" tubes (lanes 4-5) show no product; PCR is completely inhibited. Similarly, the "protoporphyin only" tubes (lanes 10-11) show no product; PCR is again completely inhibited. On the other hand, product is visible in all of the lanes (lanes 6-9) representing reactions where interfering reagent was added. The ability of transferrin and serum albumin to overcome inhibition of a non-metal-containing porphyrin suggests that this is not mediated by iron-binding.

EXAMPLE 20

In this example, the role of cofactors in the inhibitor treatment of the present invention is further demonstrated. Whole blood was prepared according to Mode III (see FIG. 1). Whole blood samples (20 μl) were lysed with protease K (0.5 mg/ml, 55° C. for 1 hour). The enzyme was inactivated by heating (95°-100° C., 10 minutes). Reactions were then set up involving the addition of bovine transferrin or serum albumin with various cofactors, including bicarbonate ion, azide ion, thiocyanate ion, cyanate ion, oxalate ion, malonate ion, glycinate ion, and thioglycolate ion. These reaction were performed at room temperature for thirty minutes. PCR was then set up using the using primer pair GH26/GH27 to produce a 242-mer product (see above). PCR was carried out for 35 cycles. The PCR products were thereafter electrophoresed (agarose) and visualized with ethidium bromide staining. A summary of the results is provided in Table 1. The presence of product bands ("+") indicated that the cofactor was, inconjunction with transferrin or serum albumin, able to overcome inhibition.

EXAMPLE 21

In this example, Mode II of the present invention was performed. Whole blood (1, 2, and 5 μl) was spotted onto a variety of membranes using micropipets (see Table 2). After spotting, each filter was air dried then sat at room temperature for 6 days prior to amplification.

The digestion and amplification experiment was run on duplicate samples of the 1 μl spot using all filters. The filters were processed as follows. Each filter was placed in a 0.5 ml eppendorph tube followed by protease K treatment. This consisted of 7.5 μl diluent, 5 μl 10X PK buffer (100 mM Tris, pH 8.0; 10 mM EDTA; 5% Tween 20; 5% NP 40), 25 μl protease K (5 mg/ml), and 12.5 μl water. The tubes were heated at 55° C. for 5' then 95° C. for 10' then cooled to room temperature. Following digestion and inactivation of the protease K, PCR and sample preparation reagents were added to each tube (10 μl 10× PCR buffer, 1.5 μl 12.5 mM dNTP stock, 1 μl 10 mM primer RS-134, 1 μl 10 mM primer RS-135, 0.5 μl 10 units/Nl Taq stock, 5 μl 0.2M NaHCO$_3$, 5μl bovine transferrin stock, and 26 μl water). The samples were then amplified (in the presence of the filter) for 35 cycles (95° C. 30''; 55° C. 30''; 72° 60'') then analyzed on a 3% Nusiev/1% agarose gel. RS-134 and RS-135 are biotinglated GH26 and GH27, respectively.

EXAMPLE 22

In this example, Mode Ib and III of the present invention was performed on panels of clinical, whole blood, HIV-serotested samples. PCR reactions were carried out using the SK38/39 system (see above). Standard control reactions were run. PCR was carried out for 35 cycles. The products were electrophoresed and viualized by oligonucleotide hybridization analysis and autoradiography. Table 3 is a summary of the data. Both Mode Ib and III results show excellent correlation with prior art techniques.

EXAMPLE 23

In this example, Mode III of the present invention was performed in comparison to boiling methods.

Experiment 1. Whole blood (200 μl) was boiled for 10 minutes then briefly centrifuged to precipitate the solid coagulated mass which formed. The supernatant layer was then used directly for PCR amplification (1, 2, 3, 4, or 5 μl), either with or without transferrin. Results showed (data not shown) that the samples without transferrin were inhibited when the sample size exceeded 1μl, while the samples with transferrin provided signal up to and including the 3 μl aliquot. This shows that transferrin relieves the effect of residual inhibitors present in the boiled only samples. An aliquot of 5 μl whole blood processed by Mode III gave a very intense signal, indicating the advantage of the method over the boiling method, which provided no signal at all with a 5 μl aliquot.

It should be stressed that the heat sensitivity of inhibitors is determined by the nature and structure of the particular inhibitor. For example, where an inhibitor is a protein, thermal denaturation occurs typically at approximately 62°-65° C. On the other hand, where an inhibitor is a protein with a prosthetic group (e.g. the prosthetic group of hemoglobin is heme), or the inhibitor is a salt (e.g. an iron salt), thermal treatment typically requires much higher temperatures.

Experiment 2. Duplicate samples of whole blood were placed in Eppendorf tubes then either boiled (in buffer) or digested with Protease K according to Mode III. The samples were then prepared for PCR (100 μl) and cycled 25, 30, 35 and 40 cycles. Both samples containing transferrin during the PCR). In all cases, the boiled samples failed to provide detectable product, while the digested (Mode III) samples provided increased signal at each point from 30 cycles on (data not shown). Adequate transferrin was present to normalize all inhibiting compounds present in the (1 μl) sample volume (when processed by Mode III).

EXAMPLE 24

Figure 20:
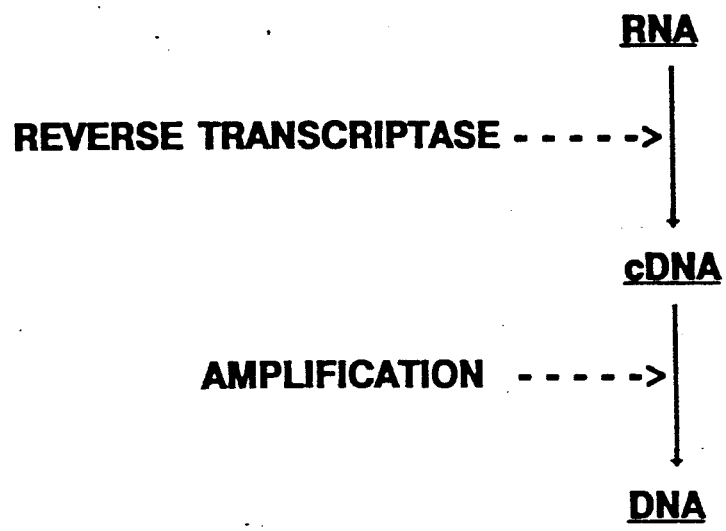
FIG. 20 schematically shows one embodiment of the method of the present invention for making deoxyribonucleic acid from ribonucleic acid according processing whole blood for amplification.

In this example, deoxyribonucleic acid was made from ribonucleic acid according to the present invention. FIG. 20 schematically shows one embodiment of the method of the present invention for making deoxyribonucleic acid (DNA) from ribonucleic acid (RNA). First, reverse transcriptase is used to make cDNA from RNA. Then amplification of the DNA is carried out.

To provide HIV-RNA for development of the sample preparation methods, the plasmid pBKBH10S, which contains the complete HIV DNA sequence (8927 bp) except for the replication region, was used as a template for in vitro HIV RNA synthesis using the T7 phage promoter. The synthesized (+) strand of HIV RNA was used as for the sample preparation experiments. Reverse transcription conditions were studied and optimized for obtaining cDNA from the RNA using avian myeloblastosis virus (AMV-RT) and random hexamer primers. PCR amplification of the cDNA was performed using primer pair SK-38/SK-39 to provide the usual 115-mer amplicon. This region encompass nucleotides 1514-1541/1628-1655 of the conserved gag region. Following PCR, the 115-mer was detected by solution oligomer hybridization using the 41-mer probe SK-19.

The step of lysing the whole blood for release of RNA for conversion to cDNA is artful. It is important to release the RNA under conditions where it is not degraded due to simultaneous release of nucleases. The protease K must degrade the nucleases faster than the nucleases degrade the RNA, or if not, there will be no "net RNA" left for transcription by RT. In this experiment, free RNA was added to whole blood, and then lysis was carried out. To minimize the RNA loss, RNAsin is added (which is a potent RNase inhibitor) during the protease K step. Salt (KCl) and DTT concentration are very important. For optimum results the following reactions conditions were found:

| RNA + Blood | RNA mix: 250 mM DTT (1 μl), 40 U/ml RNAsin (1.25 μl), 5 mg/ml protease K (2.5 μl), 10X PK buffer (2.5 μl), 1.3 ng tRNA (4.0 μl), water (3.75 μl), RNA (5.0 μl) 1 μl whole blood Digest → Δ 55° C./5' then 95°/5' |
|---|---|
| Digested Blood | RT → add 15 μl RT mix:4XRT (5 μl) |

From the above it is evident that the present invention provides a method for preparing nucleic acid samples without the accompanying difficiencies of prior art methods. The present invention provides a flexible approach to whole blood processing in that it can be carried out with i) only microliter amounts of blood (e.g. fingerstick or heelstick), ii) stored blood (including dried blood), and iii) the same, single reaction vessel used for amplification (allowing for quantitative recovery of cellular nucleic acid). The method of the present invention is also amenable to automation.

All patent publications cited in this specification are herein incorporated by reference as if each individual publication were specifically and individually indicated to be incorporated by reference.

TABLE 1

The Effect of Cofactors on Serum Albumin and Transferrin

| Cofactors | BSA | Bovine Transferrin |
|---|---|---|
| None | − | − |
| Sodium Bicarbonate (NaHCO$_3$) | + | + |
| Sodium Azide (NaN$_3$) | + | − |
| Sodium Thiocyanate (NaSCN) | + | + |
| Sodium Cyanate (NaOCN) | + | + |
| Sodium Oxalate (NaO$_2$CCO$_2$Na) | + | − |
| Sodium Malonate (NaO$_2$CCH$_2$CO$_2$Na) | + | − |
| Sodium Glycinate (NaO$_2$CH$_2$NH$_2$) | + | + |
| Sodium Thioglycolate (NaO$_2$CCH$_2$SH) | + | + |

TABLE 2

SUMMARY OF MODE II FILTER DATA

| Membrane | Size (μ) | Spotting* | Results |
|---|---|---|---|
| Pall Loprodyne | .45 | ws | Good |
| Pall Loprodyne | 1.2 | ws | Good |
| Amersham nylon | .45 | ss | Good |
| Amersham nitrocellulose | .45 | c | Good |
| Whatman #1 filter paper | | ws | Good |
| S&S PTFE (teflon) | .45 | ws (rough side) | Good |
| Pall Biodyne A (Nylon 66) | .45 | ws (1,2 μl) ss (5 μl) | Good |
| Millipore | .2 | c | Good |
| BioRad nitrocellulose | .45 | ss (5 μl = c) | Fair |
| S&S PTFE (teflon) | .2 | ws (rough side) | Fair |
| S&S nitrocellulose | .45 | ss/c | Poor |
| S&S nitrocellulose | .2 | ss/c | Poor |
| BioRad Zeta Probe | | | Poor |
| Pall Biodyne B (Nylon 66) | .45 | ws (1,2 μl) ss (5 μl) | V.Poor |

*ws = well soaked; ss = slightly soaked; c = caked on to

TABLE 3

SUMMARY OF HIV CLINICAL PANEL DATA

| Panel | Specimens | Sero-positive Specimens | Sample Prep. (min.) | PCR Method | PCR HIV(+) Specimens | False Data (+) | False Data (−) |
|---|---|---|---|---|---|---|---|
| 1 | 15 | 2 | 85 | I | 2 | 0 | 0 |
| 2 | 12 | 4 | 85 | I | 4 | 0 | 0 |
|   |    |   | 100 | II | 4 | 0 | 0 |
| 3 | 10 | 4 | 85 | I | 4 | 0 | 0 |
|   |    |   | 100 | II | 4 | 0 | 0 |
| 4 | 13 | 5 | 85 | I | 4 | 0 | 1* |
|   |    |   | 100 | II | 4 | 0 | 1 |
| 5 | 10 | 3 | 20 | II | 3 | 0 | 0 |
| 6 | 10 | 3 | 10 | II | 3 | 0 | 0 |
| 7 | 10 | 4 | 20 | I | 4 | 0 | 0 |
|   |    |   | 35 | II | 4 | 0 | 0 |
| 8 | 8 | 4 | 15 | I | 4 | 0 | 0 |

TABLE 3-continued
SUMMARY OF HIV CLINICAL PANEL DATA

| Panel | Specimens | Sero-positive Specimens | Sample Prep. (min.) | PCR Method | PCR HIV(+) Specimens | False Data (+) | False Data (−) |
|---|---|---|---|---|---|---|---|
| | | | 10 | II | 4 | 0 | 0 |

*The false negative result was confirmed both by the PCR using template DNA prepared from PBMCs isolated by the conventional Ficoll density gradient centrifugation, and by the virus culture assay.

TABLE 4
OPTIMIZED MODE Ia

| TIME | |
|---|---|
| 5 min | 50 μl whole blood in 1 ml ISOTON ® II ↓ RBC instantly lysed by lysing agent ↓ WBC pelleted by 1 min. microfuging ↓ Resuspend cells in 62.5 μl PK mix* |
| 5 min | Release DNA template Δ 55° C. |
| 5 min | Inactivate PK Δ 95–100° C. |
| total 15 min before amplification | Amplification** |

*PK mix (10 mM Tris pH 8.0, 1 mM EDTA, 0.5% Tween 20, 0.5% NP40, 2.5 mg/ml PK)
**Amplification reaction mixture contains transferrin and NaHCO$_3$: the final concentration for HCO$_3^-$ in a PCR reaction is 10 mM. The amount of transferrin used in a PCR reaction is 50 μg/1 μl blood (starting) in the PK digest. Typically, a 100 μl PCR reaction contains 20–100 μl blood.

TABLE 5
OPTIMIZED MODE Ib

| TIME | |
|---|---|
| 5 min | 50 μl whole blood in 1 ml ISOTON ® II ↓ RBC instantly lysed by lysing agent ↓ WBC pelleted by 1 min microfuging ↓ WBC washed 2X with 1 ml ISOTON ® II Cells recovered by 1 min microfuging ↓ Resuspended cells in 62.5 μl PK mix* |
| 5 min | Release DNA template Δ 55° C. |
| 5 min | Inactivate PK Δ 95–100° C. |
| total 15 min before amplification | Amplification |

*PK mix (10 mM Tris pH 8.0, 1 mM EDTA, 0.5% Tween 20, 0.5% NP40, 2.5 mg/ml PK)

TABLE 6
OPTIMIZED MODE III

| TIME | |
|---|---|
| 1 min | 5 μl whole blood 20 μl PK mix* |
| 5 min | Release DNA template Δ 55° C. |
| 5 min | Inactivate PK Δ 95–100° C. |
| total 11 min before amplification | Amplification** |

*PK mix: Made up by mixing appropriate volumes of 10x PK buffer (100 mM Tris pH 8.0, 10 mM EDTA, 5% Tween 20, 5% NP40) and stock PK (5 mg/ml), so that the final concentration of PK buffer is 1x and the final concentration of PK is 2.5 mg/ml
**Transferrin and NaHCO$_3$ are incorporated into the standard amplification reaction mixture. The final concentration for HCO$_3^-$ in a PCR reaction is 10 mM. The amount of transferrin used in a PCR reaction is 50 μg/1 μl blood in the PK digest. Typically, a 100 μl PCR reaction contains 5 μl blood.

We claim:

1. A method for preparing nucleic acid samples comprising the steps of:
   a) providing nucleic acid suspecting of containing a polymerase inhibitor; and
   b) adding transferrin to said nucleic acid to neutralize said polymerase inhibitor.

2. The method for preparing nucleic acid samples of claim 1, further comprising, after step (b), the step of amplifying said nucleic acid.

3. The method for preparing nucleic acid samples as in claim 1 wherein said transferrin is used in conjunction with one or more cofactors selected from the group consisting of bicarbonate ion, thiocyanate ion, cyanate ion, glycinate ion, thioglycolate ion, and salts thereof.

4. A method for preparing nucleic acid samples comprising the steps of:
   a) providing nucleic acid suspecting of containing a polymerase inhibitor; and
   b) adding globin to said nucleic acid to neutralize said polymerase inhibitor in the presence of a cofactor selected from the group consisting of bicarbonate ion, azide ion, thiocyanate ion, cyanate ion, oxalate ion, malonate ion, glycinate ion, thioglycolate ion and salts thereof.

5. The method for preparing nucleic acid samples of claim 4, further comprising, after step (b), the step of amplifying said nucleic acid.

6. A method for preparing nucleic acid samples comprising the steps of:
   a) providing nucleic acid suspected of containing a polymerase inhibitor; and
   b) adding serum albumin to said nucleic acid to neutralize said polymerase inhibitor in the presence of a cofactor selected from the group consisting of bicarbonate ion, azide ion, thiocyanate ion, cyanate ion, oxalate ion, malonate ion, glycinate ion, thioglycolate ion, and salts thereof.

7. The method for preparing nucleic acid samples of claim 6, further comprising, after step (b), the step of amplifying said nucleic acid.

* * * * *